US009125611B2

(12) United States Patent  (10) Patent No.: US 9,125,611 B2
Eaves  (45) Date of Patent: Sep. 8, 2015

(54) MOBILE FLUOROSCOPIC IMAGING SYSTEM

(75) Inventor: Christopher B. Eaves, Scottsdale, AZ (US)

(73) Assignee: OrthoScan, Inc., Scottsdale, AZ (US)

( * ) Notice: Subject to any disclaimer, the term of this patent is extended or adjusted under 35 U.S.C. 154(b) by 216 days.

(21) Appl. No.: 13/324,677

(22) Filed: Dec. 13, 2011

(65) Prior Publication Data

US 2012/0148031 A1  Jun. 14, 2012

Related U.S. Application Data

(60) Provisional application No. 61/422,615, filed on Dec. 13, 2010, provisional application No. 61/438,221, filed on Jan. 31, 2011.

(51) Int. Cl.
A61B 6/00 (2006.01)

(52) U.S. Cl.
CPC ............. *A61B 6/4405* (2013.01); *A61B 6/4441* (2013.01); *A61B 6/4452* (2013.01); *A61B 6/505* (2013.01); *A61B 6/588* (2013.01)

(58) Field of Classification Search
CPC .. A61B 6/4405; A61B 6/4441; A61B 6/4452; A61B 6/588
USPC ........................................................ 378/198
See application file for complete search history.

(56) References Cited

U.S. PATENT DOCUMENTS

| | | | |
|---|---|---|---|
| 2,818,510 A | 12/1957 | Hansheinrich | |
| 3,617,749 A | 11/1971 | Massiot | |
| 4,797,907 A | 1/1989 | Anderton | |
| 4,856,036 A * | 8/1989 | Malcolm et al. | .............. 378/116 |
| 4,947,414 A | 8/1990 | Stein | |
| 4,964,150 A | 10/1990 | Van Der AA | |
| 4,979,198 A | 12/1990 | Malcolm | |
| 5,038,371 A | 8/1991 | Janssen | |
| 5,040,546 A | 8/1991 | Deluhery | |
| 5,067,145 A | 11/1991 | Siczek et al. | |
| 5,111,496 A | 5/1992 | Van Es | |
| 5,148,455 A | 9/1992 | Stein | |

(Continued)

FOREIGN PATENT DOCUMENTS

| | | |
|---|---|---|
| EP | 0946082 | 9/1999 |
| EP | 0759285 | 4/2003 |

(Continued)

OTHER PUBLICATIONS

Varian, "PaxScan® 4336R Amorphous Silicon Digital X-Ray Imager", Rev. A, Oct. 2008, pp. 1-2.*

(Continued)

*Primary Examiner* — Glen Kao
*Assistant Examiner* — Chih-Cheng Kao
(74) *Attorney, Agent, or Firm* — Knobbe, Martens, Olson & Bear LLP

(57) ABSTRACT

Disclosed herein is a mobile fluoroscopic imaging system, and methods of use. A table top imaging system can include a support, an x-ray source carried by the support, an x-ray detector carried by the support and positionable at a distance from the source; a primary x-ray propagation axis extending between the source and the detector. The distance between the source and the detector can be adjustable along the axis, and the axis can be angularly adjustable throughout an angular range.

13 Claims, 24 Drawing Sheets

(56) References Cited

U.S. PATENT DOCUMENTS

| | | |
|---|---|---|
| 5,263,076 A | 11/1993 | Elff |
| 5,287,546 A | 2/1994 | Tesic |
| 5,305,368 A | 4/1994 | Bisek |
| 5,325,413 A | 6/1994 | Habraken |
| 5,422,251 A | 6/1995 | Neer et al. |
| 5,425,069 A | 6/1995 | Pellegrino et al. |
| 5,426,683 A | 6/1995 | O'Farrell, Jr. |
| 5,432,834 A | 7/1995 | Gershman |
| RE35,025 E | 8/1995 | Anderton |
| 5,475,730 A | 12/1995 | Galando |
| 5,483,960 A | 1/1996 | Steiger |
| 5,485,502 A | 1/1996 | Hinton |
| 5,499,284 A | 3/1996 | Pellegrino et al. |
| 5,503,416 A | 4/1996 | Aoki |
| 5,521,957 A | 5/1996 | Hansen |
| 5,533,084 A | 7/1996 | Mazess |
| 5,561,278 A | 10/1996 | Rutten |
| 5,577,089 A | 11/1996 | Mazess |
| 5,583,909 A | 12/1996 | Hanover |
| 5,586,162 A | 12/1996 | Grichnik |
| 5,596,779 A | 1/1997 | Meek |
| 5,608,774 A * | 3/1997 | Polichar et al. ............... 378/98.8 |
| 5,617,462 A | 4/1997 | Spratt |
| 5,627,873 A | 5/1997 | Hanover |
| 5,642,395 A | 6/1997 | Anderton |
| 5,657,369 A | 8/1997 | Stein |
| 5,687,211 A | 11/1997 | Berger |
| 5,713,357 A | 2/1998 | Meulenbrugge |
| 5,715,820 A | 2/1998 | Stein |
| 5,717,735 A | 2/1998 | Ramsdell |
| 5,729,587 A | 3/1998 | Betz |
| 5,748,704 A | 5/1998 | Mazess |
| 5,748,705 A | 5/1998 | Stein |
| 5,771,272 A | 6/1998 | Berger |
| 5,778,045 A | 7/1998 | von Stetten |
| 5,822,814 A | 10/1998 | Van der Ende |
| 5,828,221 A | 10/1998 | Habraken |
| 5,835,555 A | 11/1998 | Barry |
| 5,835,558 A | 11/1998 | Maschke |
| 5,835,562 A | 11/1998 | Ramsdell |
| 5,838,765 A | 11/1998 | Gershman |
| 5,841,832 A | 11/1998 | Mazess |
| 5,841,833 A | 11/1998 | Mazess |
| 5,850,836 A | 12/1998 | Steiger |
| 5,852,646 A | 12/1998 | Klotz |
| 5,883,935 A | 3/1999 | Habraken |
| 5,928,149 A | 7/1999 | Habraken |
| 5,949,846 A | 9/1999 | Stein |
| 5,978,439 A | 11/1999 | Koppe |
| 5,997,176 A | 12/1999 | Fairleigh |
| 6,002,959 A | 12/1999 | Steiger |
| 6,007,243 A | 12/1999 | Ergun et al. |
| 6,009,147 A | 12/1999 | Stein |
| 6,050,724 A | 4/2000 | Schmitz |
| 6,059,455 A | 5/2000 | Cabral |
| 6,067,343 A | 5/2000 | Brendler |
| 6,078,699 A | 6/2000 | Lobregt |
| 6,097,833 A | 8/2000 | Lobregt |
| 6,102,567 A | 8/2000 | Cabral |
| 6,104,780 A | 8/2000 | Hanover |
| 6,113,265 A | 9/2000 | Babler |
| 6,120,180 A | 9/2000 | Graumann |
| 6,139,183 A | 10/2000 | Graumann |
| 6,142,667 A | 11/2000 | Pattee |
| 6,144,759 A | 11/2000 | Weese |
| 6,198,806 B1 | 3/2001 | Prins |
| 6,203,196 B1 | 3/2001 | Meyer et al. |
| 6,206,566 B1 | 3/2001 | Schuetz |
| 6,217,214 B1 | 4/2001 | Cabral |
| 6,233,473 B1 | 5/2001 | Shepherd |
| 6,234,672 B1 | 5/2001 | Tomasetti |
| 6,236,712 B1 | 5/2001 | Tomasetti |
| 6,256,374 B1 | 7/2001 | Tomasetti |
| 6,275,568 B1 | 8/2001 | Prins |
| 6,282,258 B1 | 8/2001 | Stein |
| 6,282,261 B1 | 8/2001 | Mazess et al. |
| 6,282,264 B1 | 8/2001 | Smith |
| 6,364,526 B2 | 4/2002 | Ivan |
| 6,366,635 B1 | 4/2002 | Op De Beek |
| 6,379,040 B1 | 4/2002 | Hallman |
| 6,379,043 B1 | 4/2002 | Zylka |
| 6,381,298 B1 | 4/2002 | Proksa |
| 6,385,283 B1 | 5/2002 | Stein |
| 6,408,051 B2 | 6/2002 | Habraken |
| 6,426,994 B1 | 7/2002 | Van Vaals |
| 6,430,259 B2 | 8/2002 | Meek |
| 6,431,751 B1 | 8/2002 | Everett |
| 6,438,194 B2 | 8/2002 | Grass |
| 6,438,201 B1 | 8/2002 | Mazess |
| 6,442,235 B2 | 8/2002 | Koppe |
| 6,461,039 B1 | 10/2002 | Klotz |
| 6,461,040 B1 | 10/2002 | Mattson |
| 6,471,399 B1 | 10/2002 | Zylka |
| 6,473,918 B2 | 11/2002 | Schaefer |
| 6,478,802 B2 | 11/2002 | Kienzle, III |
| 6,484,049 B1 | 11/2002 | Seeley |
| 6,490,475 B1 | 12/2002 | Seeley |
| 6,496,557 B2 | 12/2002 | Wilson |
| 6,497,662 B2 | 12/2002 | Suurmond |
| 6,507,638 B2 | 1/2003 | Curtis |
| 6,542,573 B2 | 4/2003 | Schomberg |
| 6,542,770 B2 | 4/2003 | Zylka |
| 6,550,964 B2 | 4/2003 | Guerit |
| 6,554,472 B1 | 4/2003 | Dietz |
| 6,574,493 B2 | 6/2003 | Rasche |
| 6,582,120 B2 | 6/2003 | Schomberg |
| 6,582,121 B2 | 6/2003 | Crain |
| 6,587,598 B1 | 7/2003 | Devillers |
| 6,590,958 B2 | 7/2003 | Barber |
| 6,592,259 B2 | 7/2003 | Crain |
| 6,599,017 B2 | 7/2003 | Geelhoed |
| 6,606,514 B2 | 8/2003 | Grass |
| 6,608,884 B1 | 8/2003 | Mazess |
| 6,618,468 B2 | 9/2003 | Klotz |
| 6,619,840 B2 | 9/2003 | Rasche |
| 6,623,163 B2 | 9/2003 | De Vries |
| 6,637,936 B2 | 10/2003 | Crain |
| 6,644,852 B2 | 11/2003 | Crain |
| 6,654,444 B2 | 11/2003 | Grass |
| 6,659,642 B2 | 12/2003 | Hanover |
| 6,666,579 B2 | 12/2003 | Jensen |
| 6,672,032 B2 | 1/2004 | Van Der Burgt |
| 6,697,663 B1 | 2/2004 | Lin |
| 6,697,664 B2 | 2/2004 | Kienzle, III |
| 6,704,388 B2 | 3/2004 | Op De Beek |
| 6,708,054 B2 | 3/2004 | Shukla |
| 6,715,917 B1 | 4/2004 | Sohal |
| 6,718,194 B2 | 4/2004 | Kienzle, III |
| 6,733,177 B2 | 5/2004 | Pillai |
| 6,739,752 B2 | 5/2004 | Sabczynski |
| 6,740,041 B2 | 5/2004 | Faulkner |
| 6,744,852 B2 | 6/2004 | Klotz |
| 6,774,624 B2 | 8/2004 | Anderson |
| 6,788,759 B2 | 9/2004 | Op De Beek |
| 6,789,942 B2 | 9/2004 | Pillai |
| 6,813,334 B2 | 11/2004 | Koppe |
| 6,814,488 B2 | 11/2004 | Thandiackal |
| 6,814,489 B2 | 11/2004 | Jensen |
| 6,823,204 B2 | 11/2004 | Grass |
| 6,823,207 B1 | 11/2004 | Jensen |
| 6,830,375 B2 | 12/2004 | Deshpande |
| 6,831,644 B2 | 12/2004 | Lienard |
| 6,851,851 B2 | 2/2005 | Smith |
| 6,854,884 B2 | 2/2005 | Kerrien |
| 6,856,826 B2 | 2/2005 | Seeley |
| 6,856,827 B2 | 2/2005 | Seeley |
| 6,865,248 B1 | 3/2005 | Rasche |
| 6,869,217 B2 | 3/2005 | Rasche |
| 6,880,691 B2 | 4/2005 | Simmons |
| 6,887,245 B2 | 5/2005 | Kienzle, III |
| 6,892,088 B2 | 5/2005 | Faulkner |
| 6,895,076 B2 | 5/2005 | Halsmer |
| 6,917,827 B2 | 7/2005 | Kienzle, III |
| 6,922,581 B2 | 7/2005 | Kienzle, III |

(56) References Cited

U.S. PATENT DOCUMENTS

| | | |
|---|---|---|
| 6,928,142 B2 | 8/2005 | Shao |
| 6,931,093 B2 | 8/2005 | Op De Beek |
| 6,944,265 B2 | 9/2005 | Warp |
| 6,956,202 B2 | 10/2005 | Sabczynski |
| 6,959,067 B2 | 10/2005 | Rasche |
| 6,968,223 B2 | 11/2005 | Hanover |
| 6,980,921 B2 | 12/2005 | Anderson |
| 6,985,556 B2 | 1/2006 | Shanmugavel |
| 6,999,811 B2 | 2/2006 | Koppe |
| 7,001,045 B2 | 2/2006 | Gregerson et al. |
| 7,016,647 B2 | 3/2006 | Brooks |
| 7,029,175 B2 | 4/2006 | Karaus |
| 7,034,492 B2 | 4/2006 | Curtis |
| 7,052,421 B2 | 5/2006 | Simmons |
| 7,059,463 B2 | 6/2006 | Simmons |
| 7,096,148 B2 | 8/2006 | Anderson |
| 7,103,135 B2 | 9/2006 | Koppe |
| 7,108,252 B2 | 9/2006 | Jayakumaran |
| 7,123,684 B2 | 10/2006 | Jing |
| 7,123,779 B2 | 10/2006 | Beuker |
| 7,125,165 B2 | 10/2006 | Lutjens |
| 7,127,091 B2 | 10/2006 | Op De Beek |
| 7,134,786 B2 | 11/2006 | Settergren |
| 7,177,455 B2 | 2/2007 | Warp |
| 7,180,976 B2 | 2/2007 | Wink |
| 7,184,519 B2 | 2/2007 | Singh |
| 7,203,534 B2 | 4/2007 | Mollus |
| 7,263,168 B2 | 8/2007 | Singh |
| 7,277,565 B2 | 10/2007 | Rasche |
| 7,278,786 B2 | 10/2007 | Fiedler |
| 7,319,735 B2 | 1/2008 | Defreitas |
| 7,329,224 B2 | 2/2008 | Schwieker |
| 7,330,573 B2 | 2/2008 | Mielekamp |
| 7,338,207 B2 | 3/2008 | Gregerson et al. |
| 7,340,026 B2 | 3/2008 | Kohler |
| 7,342,992 B2 | 3/2008 | Schomberg |
| 7,368,888 B2 | 5/2008 | Curtis |
| 7,391,846 B2 | 6/2008 | Verdonck |
| 7,403,591 B2 | 7/2008 | Wink |
| 7,426,256 B2 | 9/2008 | Rasche |
| 7,430,272 B2 | 9/2008 | Jing |
| 7,440,535 B2 | 10/2008 | Netsch |
| 7,443,949 B2 | 10/2008 | Defreitas |
| 7,478,949 B2 | 1/2009 | Niessen |
| 7,499,525 B2 | 3/2009 | Horndler |
| 7,519,155 B2 | 4/2009 | Mollus |
| 7,530,739 B2 | 5/2009 | Lurz et al. |
| 7,539,529 B2 | 5/2009 | Schmitt |
| 7,551,758 B2 | 6/2009 | Florent |
| 7,574,026 B2 | 8/2009 | Rasche |
| 7,596,202 B2 | 9/2009 | Nielsen |
| 7,597,473 B2 | 10/2009 | Graumann et al. |
| 7,603,159 B2 | 10/2009 | Rasche |
| 7,607,832 B2 | 10/2009 | Jensen et al. |
| 7,609,806 B2 | 10/2009 | Defreitas |
| 7,628,538 B2 | 12/2009 | Dehler |
| 7,646,900 B2 | 1/2010 | Movassaghi |
| 7,650,021 B2 | 1/2010 | Braess |
| 7,654,740 B2 | 2/2010 | Behling |
| 7,657,001 B2 | 2/2010 | Van De Haar |
| 7,660,382 B2 | 2/2010 | Grass |
| 7,660,450 B2 | 2/2010 | Van De Haar |
| 7,688,940 B2 | 3/2010 | Defreitas |
| 7,706,589 B2 | 4/2010 | Rasche |
| 7,712,961 B2 | 5/2010 | Horndler |
| 7,725,153 B2 | 5/2010 | Kelly |
| 7,729,743 B2 | 6/2010 | Sabczynski |
| 7,738,626 B2 | 6/2010 | Weese |
| 7,760,853 B2 | 7/2010 | Jing |
| 7,764,984 B2 | 7/2010 | Desmedt |
| 7,766,548 B2 | 8/2010 | Dehler |
| 7,792,245 B2 | 9/2010 | Hitzke |
| 7,801,347 B2 | 9/2010 | Wilson |
| 7,804,992 B2 | 9/2010 | Wilson |
| 7,805,182 B2 | 9/2010 | Weese |
| 7,827,635 B2 | 11/2010 | Wang |
| 7,831,296 B2 | 11/2010 | DeFreitas |
| 7,835,501 B2 | 11/2010 | Hauttmann |
| 7,835,779 B2 | 11/2010 | Anderson |
| 7,845,851 B2 | 12/2010 | Rasche |
| 7,869,563 B2 | 1/2011 | Defreitas |
| 7,887,236 B2 | 2/2011 | Dehler |
| 7,907,989 B2 | 3/2011 | Borgert |
| 7,912,181 B2 | 3/2011 | Van Der Ende |
| 7,920,672 B2 | 4/2011 | Timmer |
| 7,924,968 B2 | 4/2011 | Proksa |
| 7,927,014 B2 | 4/2011 | Dehler |
| 7,949,091 B2 | 5/2011 | Jing |
| 7,970,195 B2 | 6/2011 | Ziegler |
| 7,986,765 B2 | 7/2011 | Defreitas |
| 7,991,105 B2 | 8/2011 | Mielekamp |
| 7,991,118 B2 | 8/2011 | Noordhoek |
| 8,000,435 B2 | 8/2011 | Bertram |
| 8,000,445 B2 | 8/2011 | Mollus |
| 8,021,045 B2 | 9/2011 | Foos et al. |
| 8,308,361 B2 | 11/2012 | Gregerson et al. |
| 8,622,614 B2 | 1/2014 | Carmichael et al. |
| 8,636,410 B2 | 1/2014 | Yao et al. |
| 8,678,649 B2 | 3/2014 | Bechard et al. |
| 2001/0048732 A1* | 12/2001 | Wilson et al. ............ 378/21 |
| 2004/0254456 A1 | 12/2004 | Ritter |
| 2005/0119561 A1 | 6/2005 | Kienzle, III |
| 2005/0148855 A1 | 7/2005 | Kienzle, III |
| 2005/0163279 A1 | 7/2005 | Mitschke et al. |
| 2005/0234327 A1 | 10/2005 | Saracen et al. |
| 2005/0273005 A1 | 12/2005 | Philpot |
| 2006/0120511 A1* | 6/2006 | Gregerson et al. ........ 378/198 |
| 2007/0016005 A1 | 1/2007 | Timinger |
| 2007/0025507 A1 | 2/2007 | Grass |
| 2007/0053493 A1 | 3/2007 | Bijlsma |
| 2007/0133753 A1 | 6/2007 | Jakob et al. |
| 2007/0211863 A1 | 9/2007 | Graumann et al. |
| 2007/0232897 A1 | 10/2007 | Horndler |
| 2007/0253532 A1 | 11/2007 | Van Stevendaal |
| 2007/0276243 A1 | 11/2007 | Gerard |
| 2008/0013690 A1 | 1/2008 | Lurz et al. |
| 2008/0013692 A1* | 1/2008 | Maschke ................ 378/198 |
| 2008/0020332 A1* | 1/2008 | Lavenda et al. ........ 430/495.1 |
| 2008/0021297 A1 | 1/2008 | Boosten |
| 2008/0035852 A1 | 2/2008 | Nagata et al. |
| 2008/0094396 A1 | 4/2008 | Sabczynsdi |
| 2008/0095303 A1 | 4/2008 | Grass |
| 2008/0103388 A1 | 5/2008 | Maschke et al. |
| 2008/0144904 A1 | 6/2008 | Wiegert |
| 2008/0171936 A1 | 7/2008 | Homan |
| 2008/0192997 A1 | 8/2008 | Grass |
| 2008/0199048 A1 | 8/2008 | Eck |
| 2008/0204012 A1 | 8/2008 | Krueger |
| 2008/0205723 A1 | 8/2008 | Bredno |
| 2008/0212860 A1 | 9/2008 | Schomberg |
| 2008/0218510 A1 | 9/2008 | Grass |
| 2008/0221435 A1 | 9/2008 | Rasche |
| 2008/0234570 A1 | 9/2008 | Gerard |
| 2008/0247623 A1 | 10/2008 | Delso |
| 2008/0253515 A1 | 10/2008 | Bertram |
| 2008/0260231 A1 | 10/2008 | Weese |
| 2008/0267455 A1 | 10/2008 | Grass |
| 2008/0279340 A1* | 11/2008 | Grebner et al. ............ 378/197 |
| 2008/0285721 A1 | 11/2008 | Dehler |
| 2008/0292149 A1 | 11/2008 | Rasche |
| 2008/0317311 A1 | 12/2008 | Grass |
| 2008/0318350 A1 | 12/2008 | Bhatnagar et al. |
| 2009/0010381 A1 | 1/2009 | Schlomka |
| 2009/0080751 A1 | 3/2009 | Rasche |
| 2009/0116715 A1 | 5/2009 | Bredno |
| 2009/0116717 A1 | 5/2009 | Kohler |
| 2009/0123046 A1 | 5/2009 | Mielekamp |
| 2009/0154787 A1 | 6/2009 | Bertram |
| 2009/0161815 A1 | 6/2009 | Grass |
| 2009/0169080 A1 | 7/2009 | Noordhoek |
| 2009/0202127 A1 | 8/2009 | Bertram |
| 2009/0281418 A1 | 11/2009 | Ruijters |
| 2009/0316973 A1 | 12/2009 | Movassaghi |
| 2010/0001156 A1 | 1/2010 | Stefan |

(56) References Cited

U.S. PATENT DOCUMENTS

| | | |
|---|---|---|
| 2010/0014631 A1 | 1/2010 | Sonsky |
| 2010/0014726 A1 | 1/2010 | Schaefer |
| 2010/0014740 A1 | 1/2010 | Movassaghi |
| 2010/0020161 A1 | 1/2010 | Bertrams |
| 2010/0020928 A1 | 1/2010 | Van De Haar |
| 2010/0027742 A1 | 2/2010 | Movassaghi |
| 2010/0049038 A1 | 2/2010 | Florent |
| 2010/0054422 A1 | 3/2010 | Ohmura et al. |
| 2010/0061603 A1 | 3/2010 | Mielekamp |
| 2010/0061610 A1 | 3/2010 | Van De Haar |
| 2010/0067649 A1 | 3/2010 | Noordhoek |
| 2010/0074485 A1 | 3/2010 | Movassaghi |
| 2010/0094124 A1 | 4/2010 | Schoonenberg |
| 2010/0094128 A1 | 4/2010 | Manzke |
| 2010/0098315 A1 | 4/2010 | Hansis |
| 2010/0104161 A1 | 4/2010 | Ziegler |
| 2010/0111261 A1 | 5/2010 | Maack |
| 2010/0111385 A1 | 5/2010 | Hummel |
| 2010/0145193 A1 | 6/2010 | Florent |
| 2010/0158318 A1 | 6/2010 | Snoeren |
| 2010/0168556 A1 | 7/2010 | Shen |
| 2010/0172472 A1 | 7/2010 | Ermes |
| 2010/0172541 A1 | 7/2010 | Homan |
| 2010/0189337 A1 | 7/2010 | Jandt |
| 2010/0189376 A1 | 7/2010 | Bertram |
| 2010/0191094 A1* | 7/2010 | Bowers et al. ............... 600/411 |
| 2010/0194750 A1 | 8/2010 | Mielekamp |
| 2010/0201786 A1 | 8/2010 | Schaefer |
| 2010/0208971 A1 | 8/2010 | Neukirchen |
| 2010/0215213 A1 | 8/2010 | Mielekamp |
| 2010/0226537 A1 | 9/2010 | Villain |
| 2010/0234719 A1 | 9/2010 | Kelly |
| 2010/0239073 A1 | 9/2010 | Eaves |
| 2010/0239140 A1 | 9/2010 | Ruijters |
| 2010/0246888 A1 | 9/2010 | Bontus |
| 2010/0264324 A1 | 10/2010 | Hoornaert |
| 2010/0266104 A1 | 10/2010 | Van Der Ende |
| 2010/0266220 A1 | 10/2010 | Zagorchev |
| 2010/0290583 A1 | 11/2010 | Noordhoek |
| 2010/0290584 A1 | 11/2010 | Vesel |
| 2010/0295846 A1 | 11/2010 | Schaefer |
| 2010/0308229 A1 | 12/2010 | Bertram |
| 2010/0316270 A1 | 12/2010 | Erhard |
| 2010/0322380 A1 | 12/2010 | Baeumer |
| 2010/0331782 A1 | 12/2010 | Hendriks |
| 2011/0002444 A1 | 1/2011 | Schmitt |
| 2011/0002517 A1 | 1/2011 | Mollus |
| 2011/0007874 A1 | 1/2011 | Vogtmeier |
| 2011/0069808 A1 | 3/2011 | DeFreitas |
| 2011/0087132 A1 | 4/2011 | DeFreitas |
| 2011/0095197 A1 | 4/2011 | Forthmann |
| 2011/0110573 A1 | 5/2011 | Wiegert |
| 2011/0116598 A1 | 5/2011 | Gotman |
| 2011/0122999 A1 | 5/2011 | Vogtmeier |
| 2011/0135053 A1 | 6/2011 | Noordhoek |
| 2011/0158479 A1 | 6/2011 | Homan |
| 2011/0168878 A1 | 7/2011 | Hoerndler |
| 2011/0182492 A1 | 7/2011 | Grass |
| 2011/0192997 A1 | 8/2011 | Vogtmeier |
| 2012/0143625 A1 | 6/2012 | Eaves et al. |
| 2012/0300909 A1 | 11/2012 | Simmons et al. |
| 2013/0003939 A1 | 1/2013 | Bouvier et al. |
| 2014/0093045 A1 | 4/2014 | Shimada et al. |

FOREIGN PATENT DOCUMENTS

| | | |
|---|---|---|
| WO | WO 99/29144 | 6/1999 |
| WO | WO 2014/088193 | 6/2014 |

OTHER PUBLICATIONS

Apr. 13, 2012 International Search Report for PCT/US2011/064741 in 13 pages.

XiTec XiScan 1000 Mini C-arm unit: Update Evaluation, Health Devices, vol. 25, No. 11, pp. 413-425 (Nov. 1999).

* cited by examiner

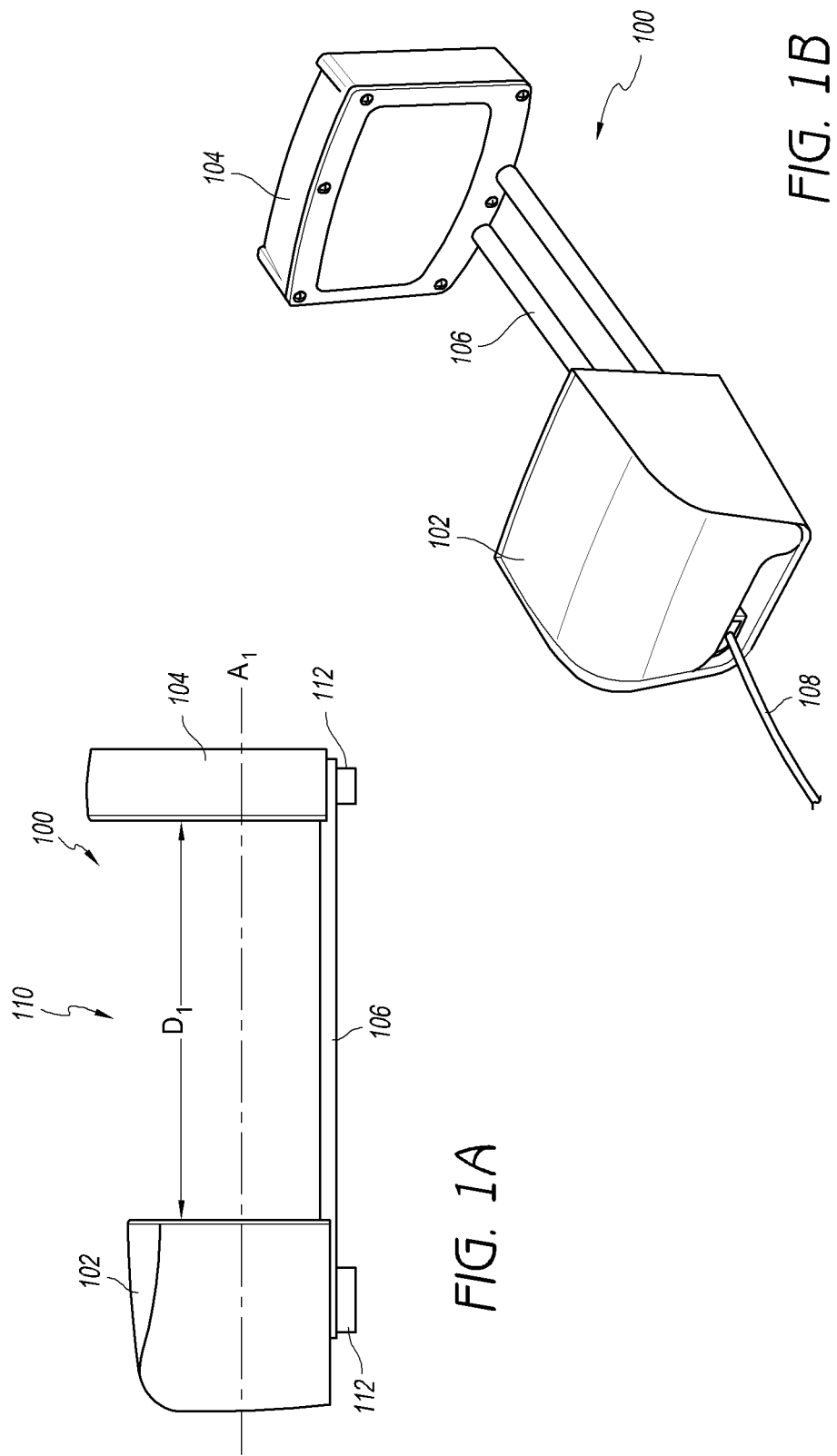

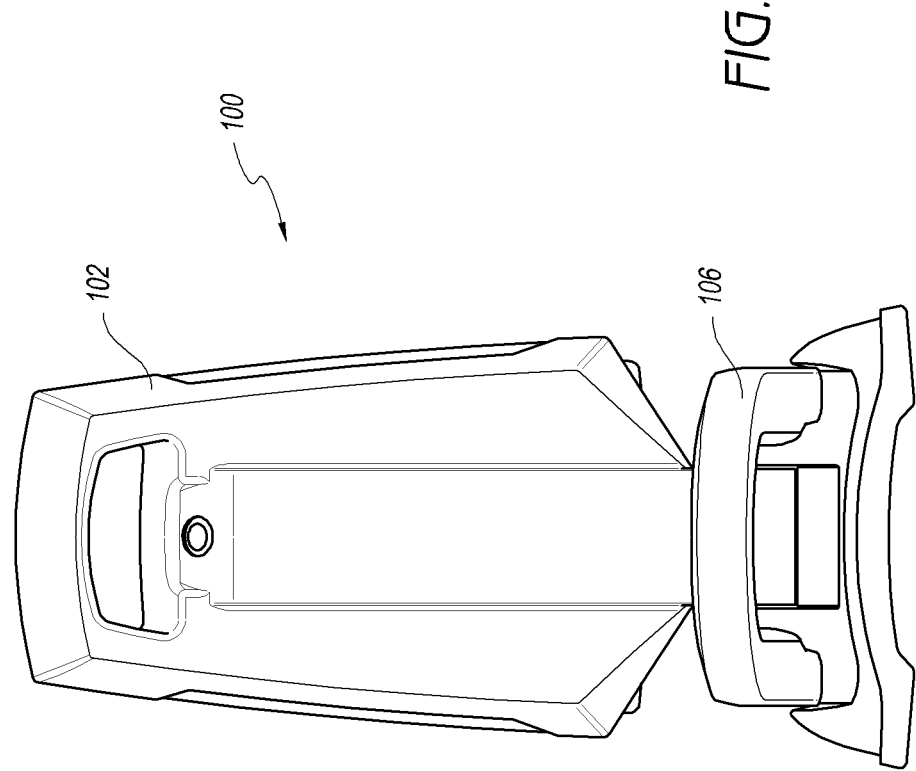

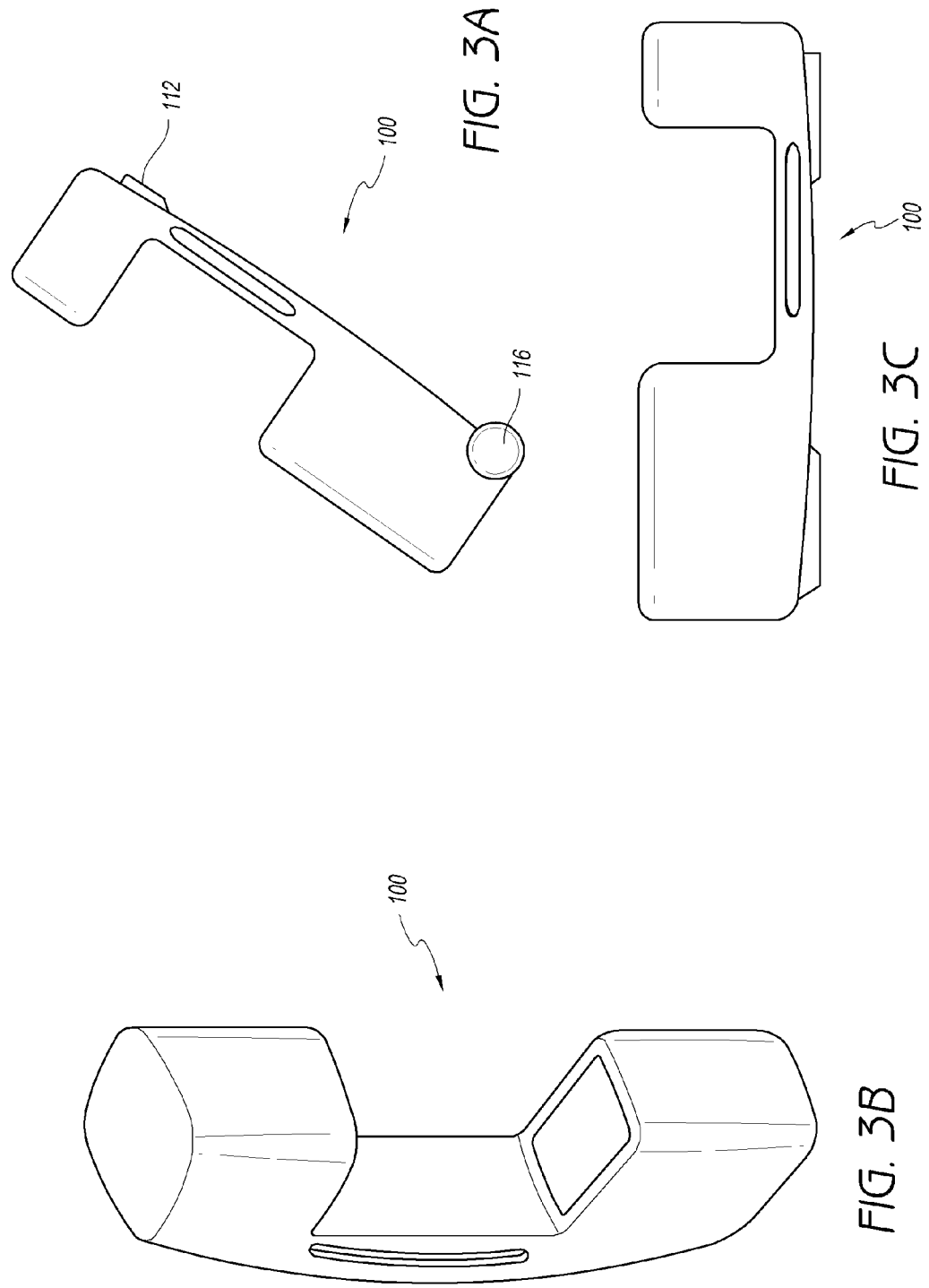

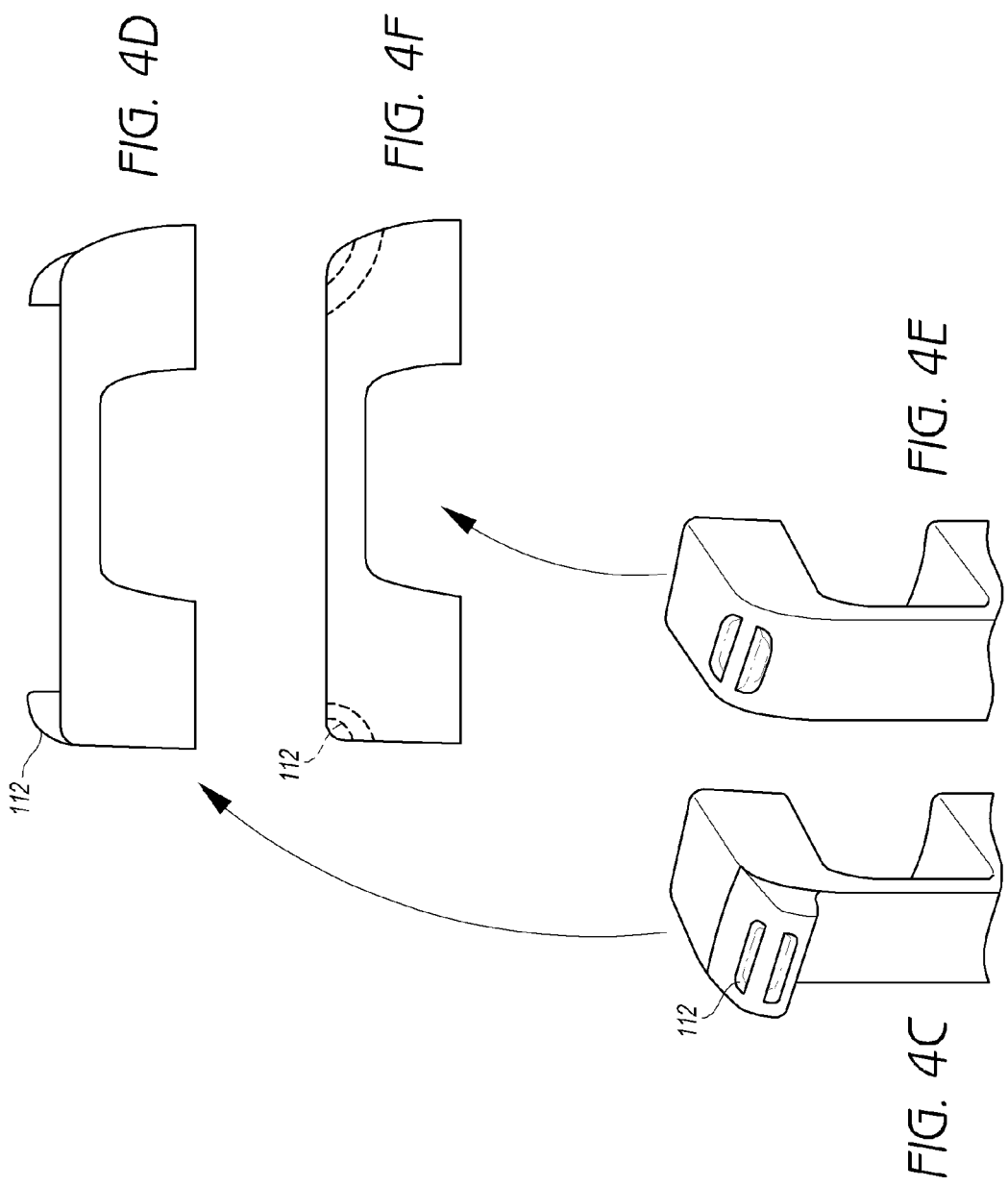

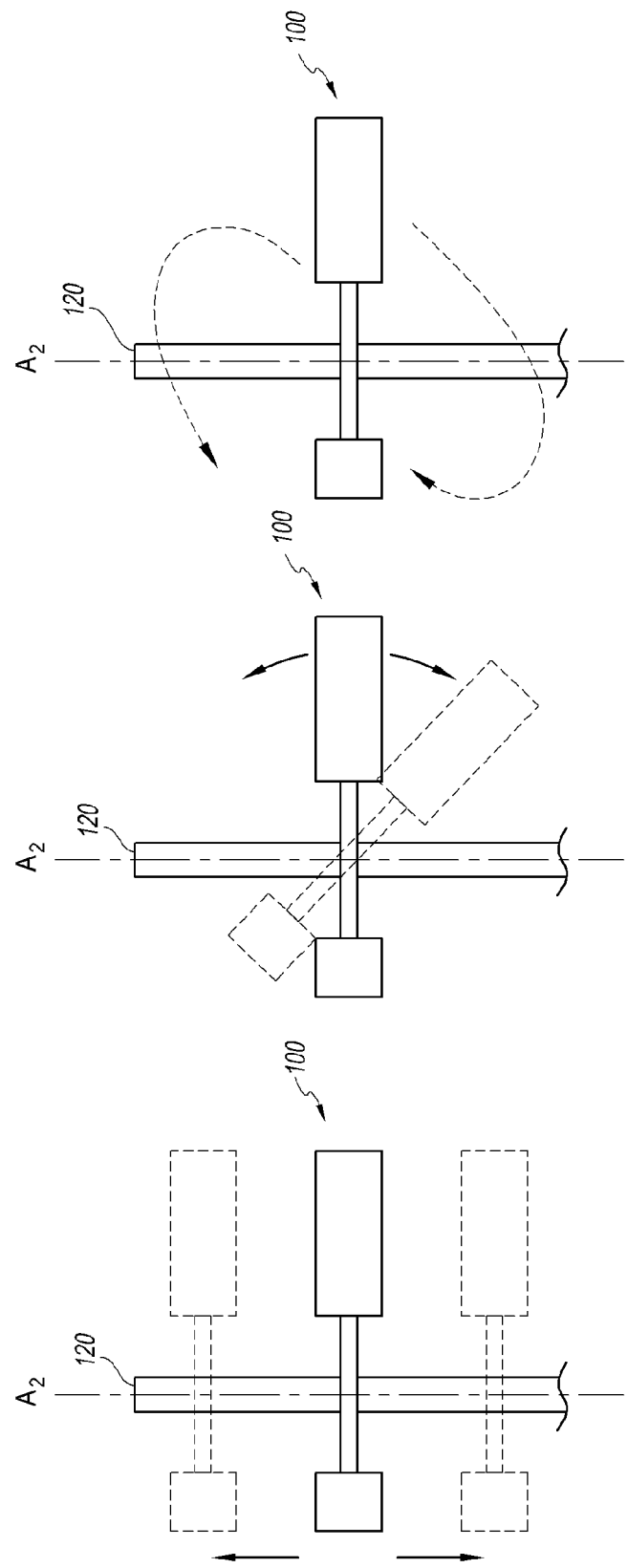

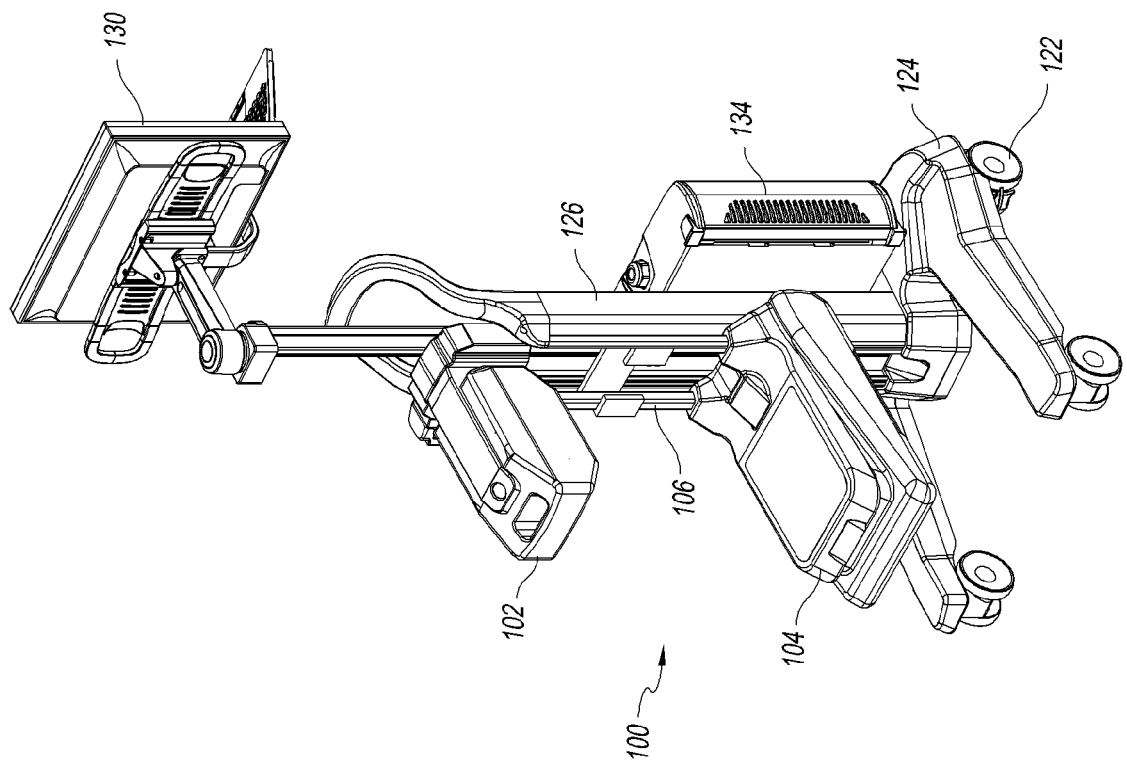

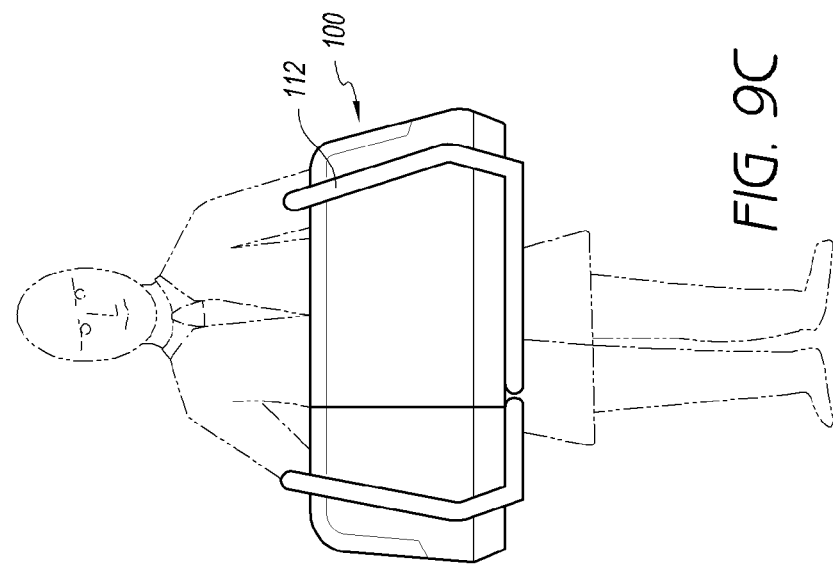
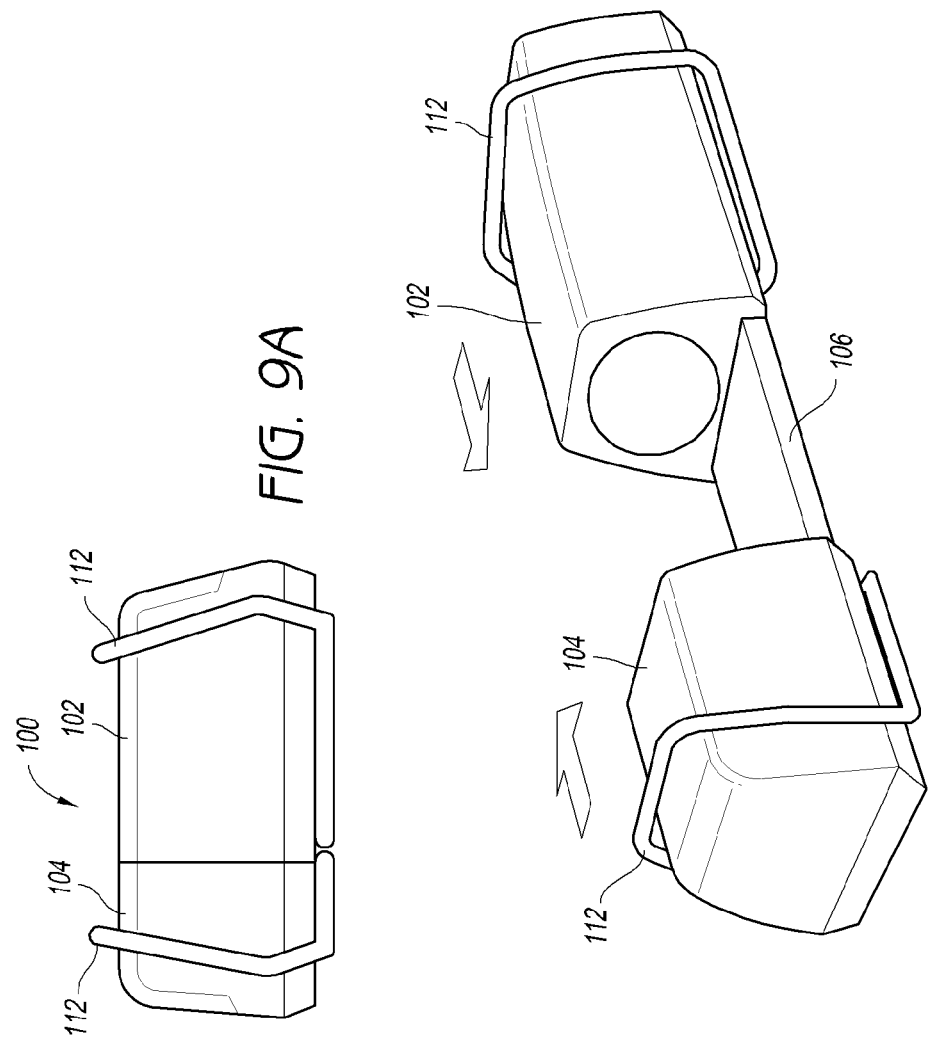
FIG. 9A  FIG. 9B  FIG. 9C

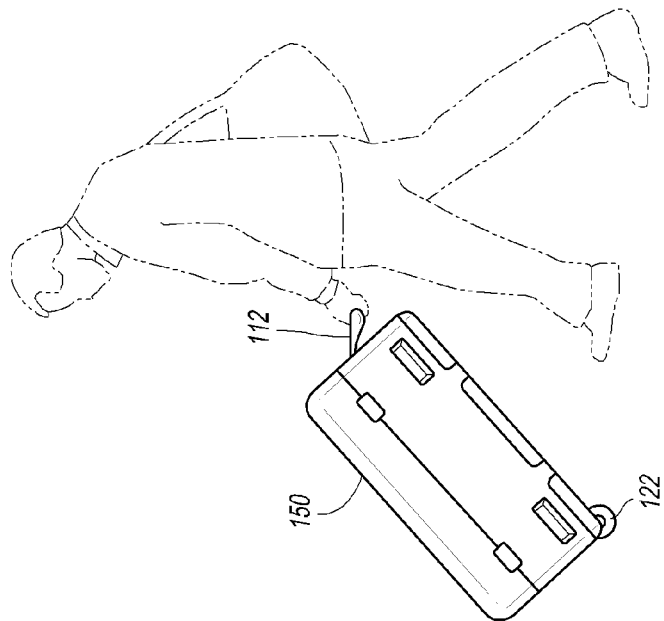
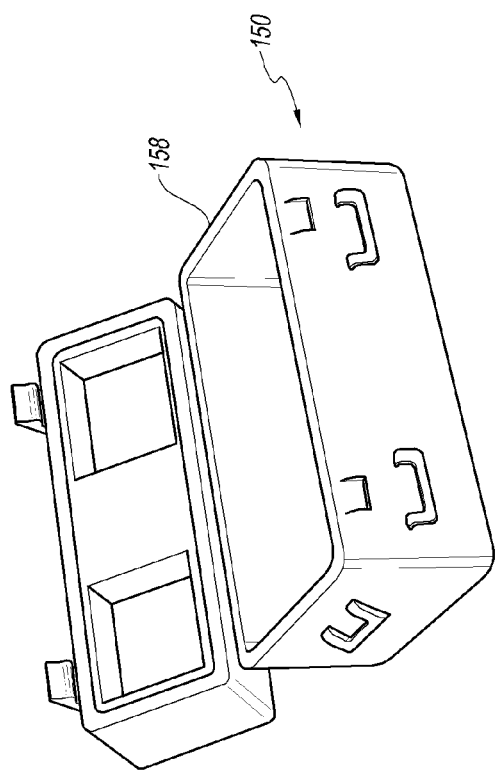
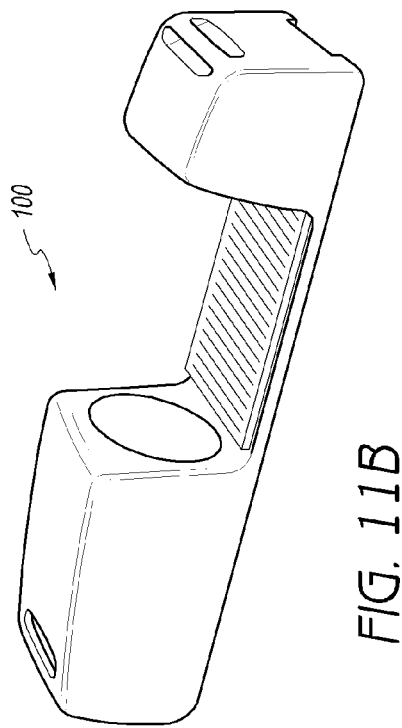

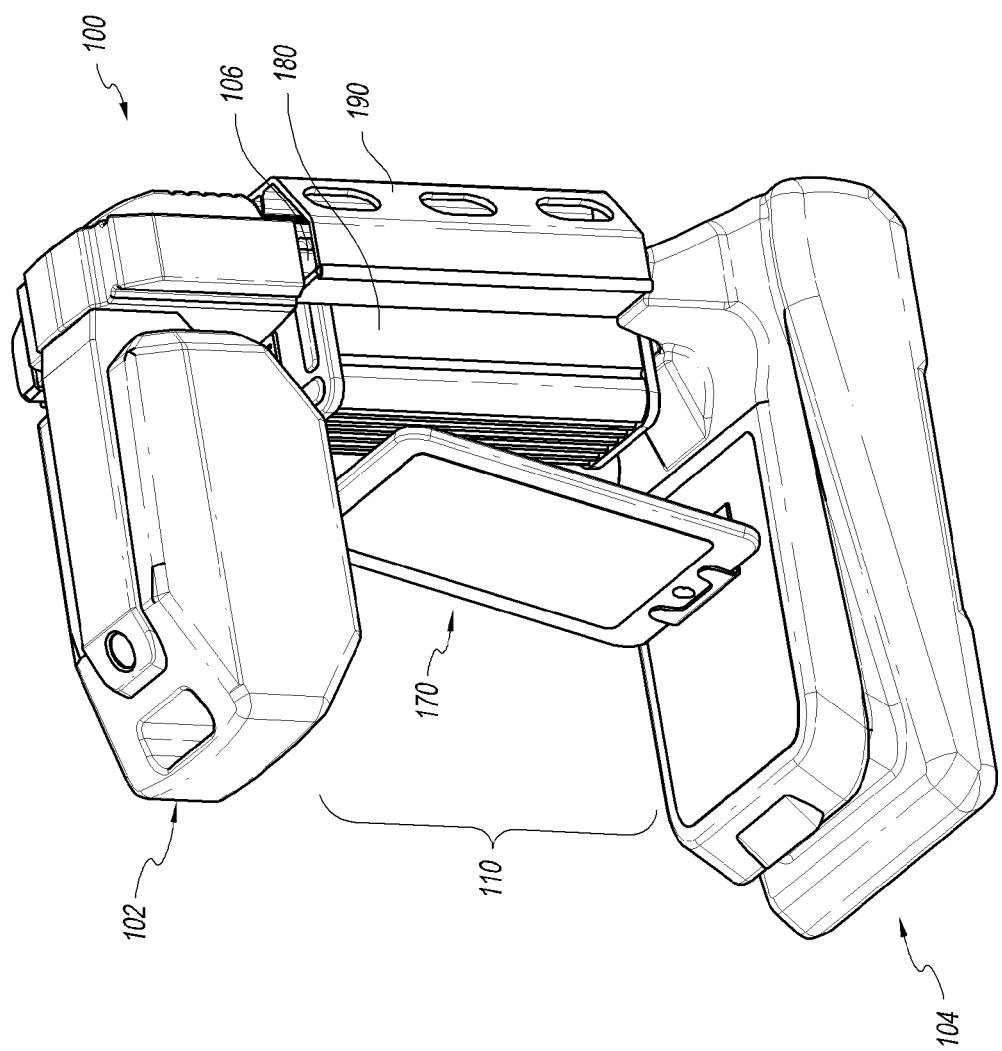

MOBILE FLUOROSCOPIC IMAGING SYSTEM

PRIORITY CLAIM

This applications claims the benefit under 35 U.S.C. §119 (e) as a nonprovisional application of U.S. Prov. App. No. 61/422,615 filed on Dec. 13, 2010 and U.S. Prov. App. No. 61/438,221 filed on Feb. 28, 2011, both of which are hereby incorporated by reference in their entireties.

BACKGROUND

1. Field of the Invention

The invention relates in some aspects to a mobile imaging system, and accessory components for a mobile imaging system.

2. Description of the Related Art

Mini C-arm units are compact fluoroscopic imaging systems designed for real-time imaging of, for example, extremities. However, what is needed are systems with superior form factors and modular configurations for improved mobility and imaging flexibility.

SUMMARY

In some embodiments, disclosed herein is a portable, reconfigurable imaging system that can advantageously be placed on a tabletop surface, for example. The system can include a support, an x-ray source carried by the support, an x-ray detector carried by the support and positionable at a distance from the source, a primary x-ray propagation axis extending between the source and the detector, a first surface on an opposite side of the source from the detector, a second surface on an opposite side of the detector from the source, and at least a third surface generally parallel to the axis. The system can be stably placed on a horizontal surface on either of the first or second surfaces such that the axis extends generally vertically, or on the third surface such that the axis extends generally horizontally. The distance along the axis between the source and the detector can either be fixed or adjustable. The detector can be a flat detector in some embodiments. The system can also include a connector, for removable connection to a cart. The system can also include a monitor, which can be either connected via wires or wirelessly to the detector. The system can also include at least a first control panel on the source, and at least a second control panel on at least one of the detector and the support. The source can be configured to produce a pulsed x-ray beam.

Also disclosed herein is a mobile imaging system, that can include a support, an x-ray source carried by the support, and a flat panel detector carried by the support, wherein the flat panel detector is positionable between a table and a patient's knee when the patient is in a supine position on the table. The system can, in some embodiments, weigh no more than about 70 pounds, 60 pounds, 50 pounds, 40 pounds, 30 pounds, 20 pounds, or less. In some embodiments, the flat panel detector has a thickness of less than about 20 cm, 18 cm, 16 cm, 14 cm, 12 cm, 10 cm, 8 cm, 6 cm, or even less.

In some embodiments, disclosed is a table top imaging system, including an x-ray source carried by the support, an x-ray detector carried by the support and positionable at a distance from the source, and a primary x-ray propagation axis extending between the source and the detector. The distance between the source and the detector is adjustable along the axis, and the axis is angularly adjustable throughout an angular range. In some embodiments, the angular range can be, for example, at least about 15, 30, 45, 60, 75, 90, 105, 120, 135, 150, 165, 180, or more degrees.

BRIEF DESCRIPTION OF THE DRAWINGS

FIGS. 1A-1E illustrate various views of a core mobile imaging system that includes an x-ray source assembly, a detector assembly, and a connecting element operably connecting the x-ray source assembly and the detector assembly.

FIG. 2A is an end view of a core mobile imaging system, illustrating the external face of the x-ray source assembly and connecting element.

FIG. 3A illustrates the portability of the core mobile imaging system, that could include one or more wheels in some embodiments.

FIGS. 3B and 3C illustrates a core mobile imaging system ready for imaging and having the longitudinal axis of the system vertically and horizontally oriented, respectively.

FIGS. 4C-4F illustrate handles, or grip points for use in lifting or moving the core mobile imaging system.

FIGS. 6A-6C schematically illustrate non-limiting examples of possible degrees of freedom the core mobile imaging system with respect to the elongate member of the cart, according to some embodiments of the invention.

FIG. 8A illustrates an embodiment of a core mobile imaging system in a generally vertical orientation and attached to elongate member of cart, similar to that described and illustrated in connection with FIG. 5B.

FIGS. 9A-9C illustrate that the core mobile imaging system can move from a first axially enlarged (open) configuration as illustrated in FIG. 9B during operation to a second axially reduced (closed) configuration in the direction of arrows of FIG. 9B, as illustrated in FIGS. 9A and 9C for convenient transport and/or storage.

FIG. 11A illustrates another embodiment of a case that may have a protective insert that may be made of foam or similar material for the imaging system shown in FIG. 11B and previously described. FIG. 11C illustrates the imaging system within case being rolled by a transporter using wheels and handle.

FIG. 13C illustrates one possible embodiment of a transport or storage configuration for a core mobile imaging system, with the wireless remote viewer/control and external power unit stored in the space in between the x-ray source assembly and the detector assembly.

DETAILED DESCRIPTION

Figure 1C:
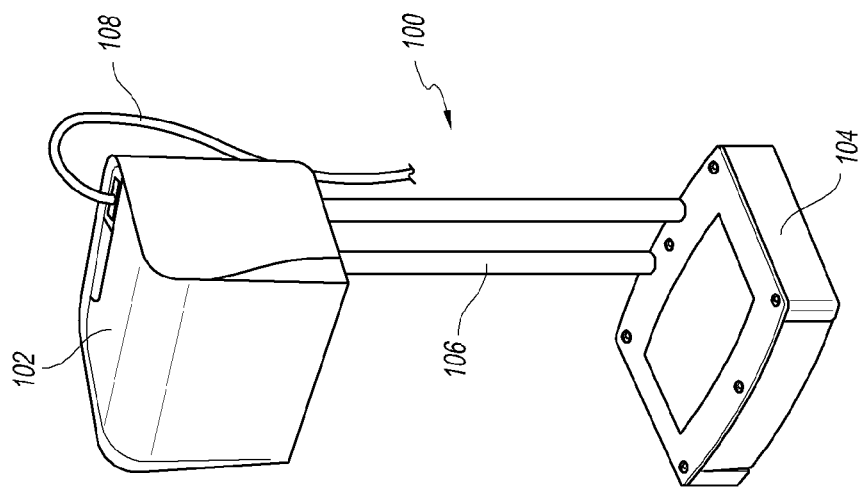
Figure 1D:
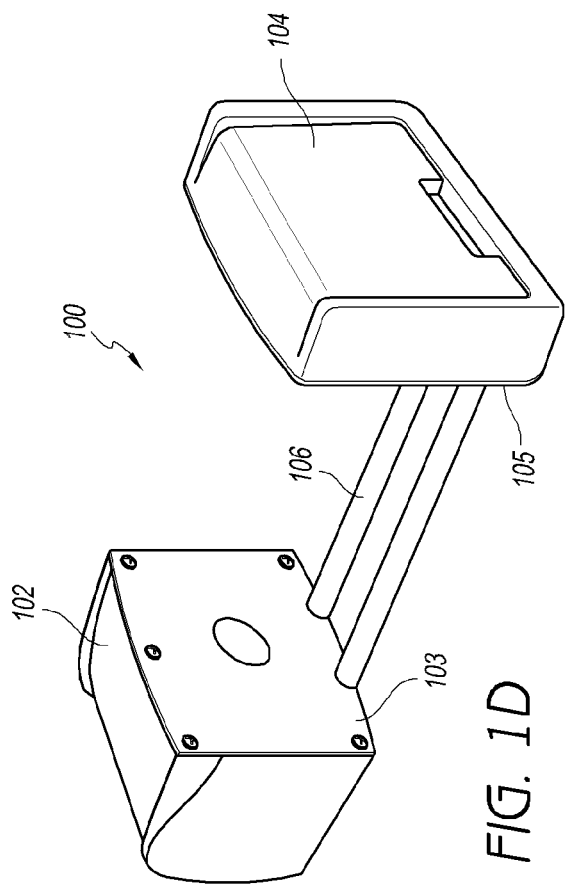

Disclosed herein are mobile digital imaging systems capable of fluoroscopic x-ray and static x-ray imaging. The device can provide an imaging solution similar to that of a mobile C-arm, but with an improved mechanical form factor focused on, for example, the mobility of the system, and the versatility of its application. In some embodiments, instead of an arcuate C-arm, the system includes a backing component that could be relatively linear to connect an x-ray source assembly and a detector assembly (that could be non-arcuate or include stable base elements) such that the system can lie in a stable position in various vertical and/or horizontal orientations, e.g., on a tabletop. As such the core system could have, notwithstanding the space required for an anatomical structure to be imaged between the x-ray source and the detector, a generally cubical or rectangular prism-type profile. The system can also be modularly reversibly attachable to a cart or wall mount, and move in at least one, two, three, or more degrees of freedom relative to the cart or wall mount. In this regard, the core imaging system can be movable axially, or rotate in one, two, or more axes relative to the cart or wall mount. The core imaging system can be axially reducible, such as along its length to allow for a smaller footprint for storage and also to vary the source to intensifier distance when clinically desirable.

The core mobile imaging system provides a lightweight imaging device that can be transported easily from location to location, as well as within a location such as a physician's office, ambulatory surgical center, operating room, hospital ward, or emergency department for example, without using specialized mechanical transport such as a van or truck or a vehicle fitted with a special mechanical lift device for the unit. The imaging system can also be used for both diagnostic and therapeutic field applications such as in vehicles such as an ambulance, ship, plane, helicopter, and the like; in a military theater; in a stadium for athletic events; at a construction or other industrial site; in a natural or man-made disaster area; or in an underserved or third world community, to give a few examples.

In some embodiments, the core mobile imaging system can weigh less than about 100, 75, 60, 50, 40, 30 or less pounds and could be powered by a small portable power source or standard AC current. The system can allow the user to view images on a screen connected via a wired connection or wireless protocol including USB, FireWire, Bluetooth, infrared, Wi-Fi, cellular, or other connection to, for example, a tablet computer, desktop or laptop computer, mobile phone, television, projector, or specialized medical-grade monitor. The system could also interface with a Digital Imaging and Communications in Medicine (DICOM), Picture Archiving and Communication System (PACS), or other electronic medical record system. The core mobile imaging system can optionally be mounted to several accessory components to provide positioning assistance based on the specific needs of the user. These accessory components may or may not be mobile, and may or may not be transported with the core mobile imaging system.

FIGS. 1A-1E illustrate various views of a core mobile imaging system 100 that includes an x-ray source assembly 102, a detector assembly 104, and a connecting element 106 operably connecting the x-ray source assembly 102 and the detector assembly 104. The x-ray source assembly 102 and the detector assembly can be separated by a distance D1. While distance D1 can be fixed, in some embodiments, one or both of the x-ray source assembly 102 and the detector assembly 104 are movable along the longitudinal axis A1 of the core mobile imaging system 100 to increase or decrease distance D1 according to the patient's anatomy, size, and desired imaging. As such, the maximal fixed or variable distance D1 could be between about 12 inches to about 48 inches, or between about 12 inches to about 24 inches in some embodiments. The distance D1 could be zero or near zero in an adjustable system where either or both of the x-ray source assembly 102 and detector assembly 104 are axially movable with respect to each other. The space 110 between x-ray source assembly 102 and detector assembly 104 is reserved for an item, such as a body part such as a hand, wrist, forearm, elbow, humerus, shoulder, skull, cervical, thoracic, lumbar, or sacral spine, hip, femur, knee, leg, ankle, or foot, to be imaged. In some embodiments, the space 110 could be between about 20 cm and 60 cm, or between about 25 cm and about 30 cm in length between the x-ray source assembly and the detector assembly 104. The width of the space 110 could be between about 30 cm to about 90 cm, between about 45 cm to about 75 cm, or about 60 cm in some embodiments. In some embodiments, the space 110 is generally cubical. The imaging system 100 can also include one, two, or more handles 112 for ease in transport, such as attached to the x-ray source assembly 102 and/or detector assembly 104 along the posterior side of the imaging system 100 as illustrated in FIG. 1A. In some embodiments, the imaging system 100 has a major axis end-to-end distance (length) that is at least about 110%, 120%, 130%, 140%, 150%, 175%, 200%, or more of a minor axis (width) side-to-side distance. In some embodiments, the core mobile imaging system 100 has a length of between about 90 cm to about 250 cm, or between about 120 cm and about 190 cm; a width of between about 30 cm to about 75 cm, or between about 45 cm to about 75 cm; and/or a height of between about 30 cm to about 75 cm, or between about 45 cm to about 75 cm measured when the system 100 is positioned on a flat surface with its longitudinal axis oriented horizontally.

Figure 1E:
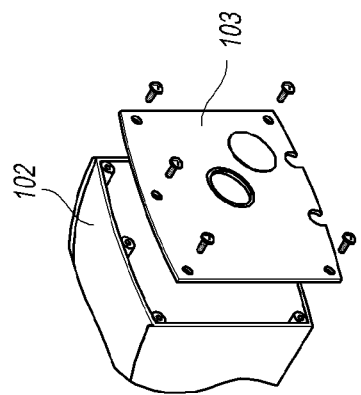

The core mobile imaging system 100 may include a power source, such as a battery that can be contained within the x-ray source assembly 102 in some embodiments. The x-ray source assembly 102 can include one, two, or more conduits 108 for battery charging, to transmit external power such as AC power, and/or as a data link for the core mobile imaging system 100. As illustrated in FIG. 1E, medial surface panel 103 of the x-ray source assembly 102 (and/or the detector assembly 104—not shown) can be opened using screws, attached using hinges akin to a door, or other mechanism to access a battery or other internal components. In some embodiments, the x-ray source assembly 102 includes a generator that has a peak kilovoltage (kVp) of between about 40 kVp to about 70 kVp, and a tube current of between about 25 to about 150 µA. In some embodiments, the system includes an automatic brightness stabilization component. The focal spot of an X-ray tube of the system could be, in some embodiments, between about 0.05 mm to about 0.50 mm.

The detector assembly 104 can be a flat detector design in some embodiments. The flat panel image receptor generally includes a planar substrate such as glass laminated with an array of sensors such as amorphous silicon crystals that convert x-ray energy to electrical signals. That is, the sensors emit an electric potential when struck by photons of x-ray energy. The magnitude of the potential is related to the intensity of the x-ray beam. The electrical signals can be read out from a row/column matrix and then converted to digital data. In one embodiment, the flat panel image receptor can include a Cesium Iodide scintillating layer on an amorphous silicon glass substrate. The scintillating layer converts x-ray energy into light. An array of photodiodes on the glass substrate convert the light into electrical signals. The electrical signals are read out of a row/column matrix that is accessed using thin film transistor switches on the amorphous silicon substrate. The analog data is then converted to a digital format for downstream processing. Suitable amorphous silicon-based, flat panel image receptors are described, for example, in U.S. Pat. Nos. 5,079,426; 5,117,114; 5,164,809; and 5,262,649 which are hereby incorporated by reference in their entireties. The flat panel image receptor can be of any dimension such as, for example, 20 cm×25 cm, and the system can be easily upgraded to incorporate larger flat panel image receptors. In some embodiments, the flat panel image receptor has a dimension, such as a thickness, of no more than about 30 cm, 25 cm, 20 cm, 18 cm, 16 cm, 14 cm, 12 cm, 10 cm, 8 cm, 6 cm, 4 cm, or less.

The connecting element 106 may include one, two, or more members, such as rods (two rods shown in FIGS. 1B-1D) or a discrete end panel that may be rectangular, for example, and extend partially or entirely along a surface of the x-ray source assembly 102 and the detector assembly 104. The connecting element 106 could be integrally formed or otherwise attached to the x-ray source assembly 102 and the receptor assembly 104. While the connecting element 106 could include an arcuate C-arm, in some embodiments the connecting element is generally linear and follows the straight-line distance between the medial surface 103 of the x-ray source assembly 102 and the medial surface 105 of the detector assembly 104. In other words, the connecting element 106 along its axial length can be generally parallel to the longitudinal axis of the core mobile imaging system A1.

A generally linear connecting element 106, or a system with linear surfaces (e.g., feet or one, two, three, or more flat or relatively flat surfaces of the x-ray source assembly 102 and/or receptor assembly 104) akin to a rectangular or square box for example, can be advantageous in that it can allow the core mobile imaging system 100 to be able to stably rest in several configurations based on the geometry of the outer housings of the unit. In contrast, a conventional C-arm or mini C-arm could not be stably positioned with the C-arm resting on the flat surface, but would instead rock back and forth or possibly fall on its side. Furthermore, the systems, such as those described herein have a smaller overall footprint and such can be more easily transported and stored. In some embodiments, the core mobile imaging system can stand on top of a flat surface such as a desk, table, floor, etc. in several positions such as upright, (with the longitudinal axis A1 of the device aligned vertically) with the x-ray source assembly 102 superior to (above) the receptor assembly 104 as illustrated in FIG. 1C; upside-down with the x-ray source assembly 102 inferior to (below) the receptor assembly 104; flat (with the longitudinal axis A1 of the device aligned horizontally) with the x-ray source assembly 102 located in a lateral position to the image receptor assembly 104 with the handles 112 facing upward; in a lateral decubitus position (with the longitudinal axis A1 of the device aligned horizontally) with the x-ray source assembly 102 located in a lateral position to the image receptor assembly 104 with the handles 112 facing the front (or facing the user position); or in a lateral decubitus position (with the longitudinal axis A1 of the device aligned horizontally) with the x-ray source assembly 102 located in a lateral position to the image receptor assembly with the handles 112 facing the back (or facing the imaging target). The connecting element 106 need not be entirely linear so long as the system 100 is stable when positioned, for example, on a tabletop.

Figure 2B:
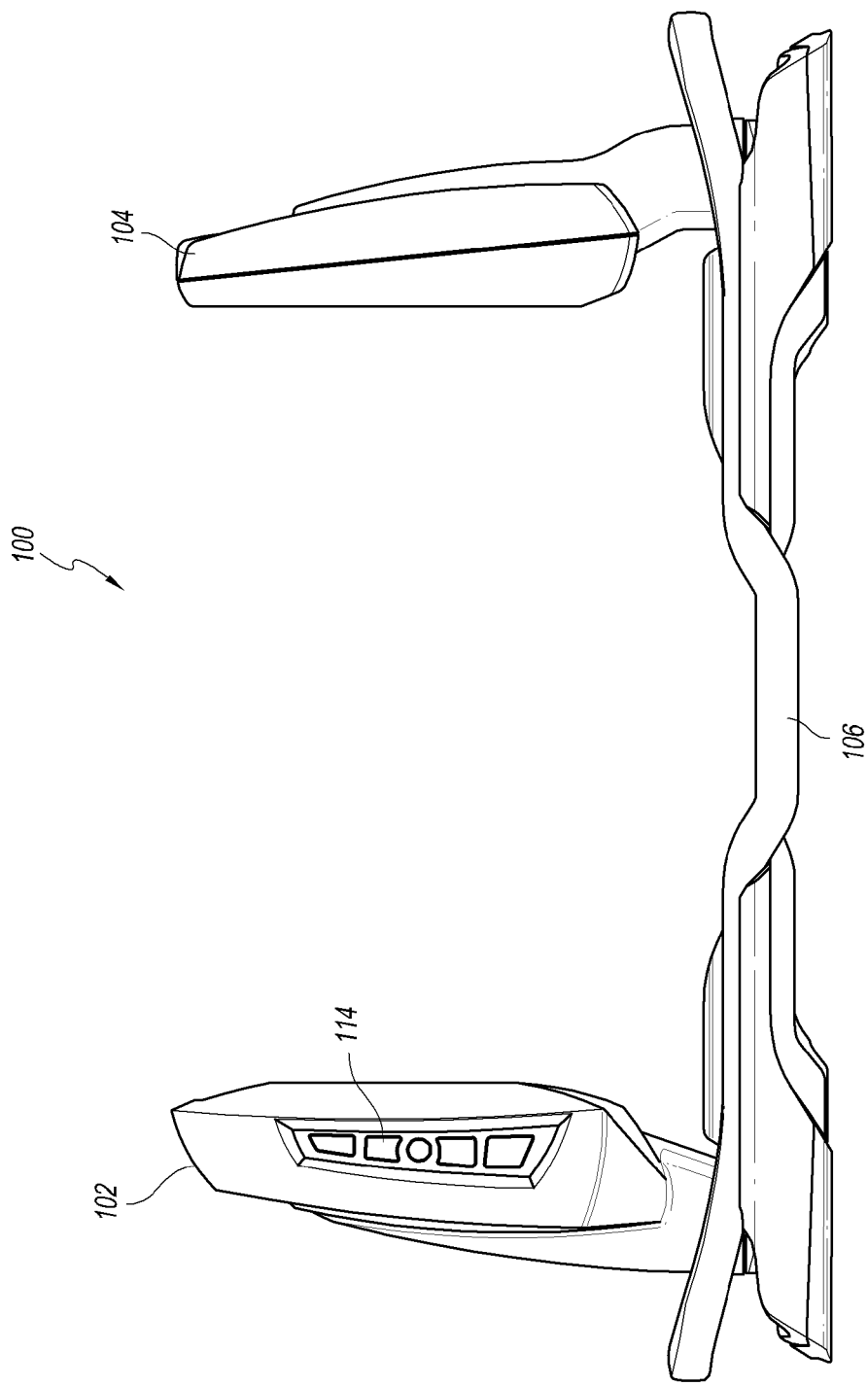
FIG. 2B illustrates a side view of a horizontally oriented imaging system, also showing a control panel on the x-ray source assembly.

FIG. 2A is an end view of a core mobile imaging system 100, illustrating the external face of the x-ray source assembly 102 and connecting element 106. FIG. 2B illustrates a side view of a horizontally oriented imaging system 100, also showing a control panel 114 on the x-ray source assembly 102. In other embodiments, the control panel 114 can be located on the detection assembly 104, connecting element 106, or elsewhere on the imaging system 100. The control panel 114 can include one, two, or more functions for operating the imaging system 100 including, for example, fluoro, rotate, anterior-posterior and lateral image hold, kv/mA (bright/dark), print, save, and the like. When activated using, for example, the control console, the diagnostic imaging system, and, in particular, the x-ray source exposure can be either continuous or pulsed. In the pulsed mode, radiography procedures can be performed, such as CINE, Spot Film and DSA, thereby generating radiographic image representations. The x-ray source can be gated on and off in the pulsed mode using a conventional grid control circuitry or a pulse fluoro high-voltage power supply.

Figure 2C:
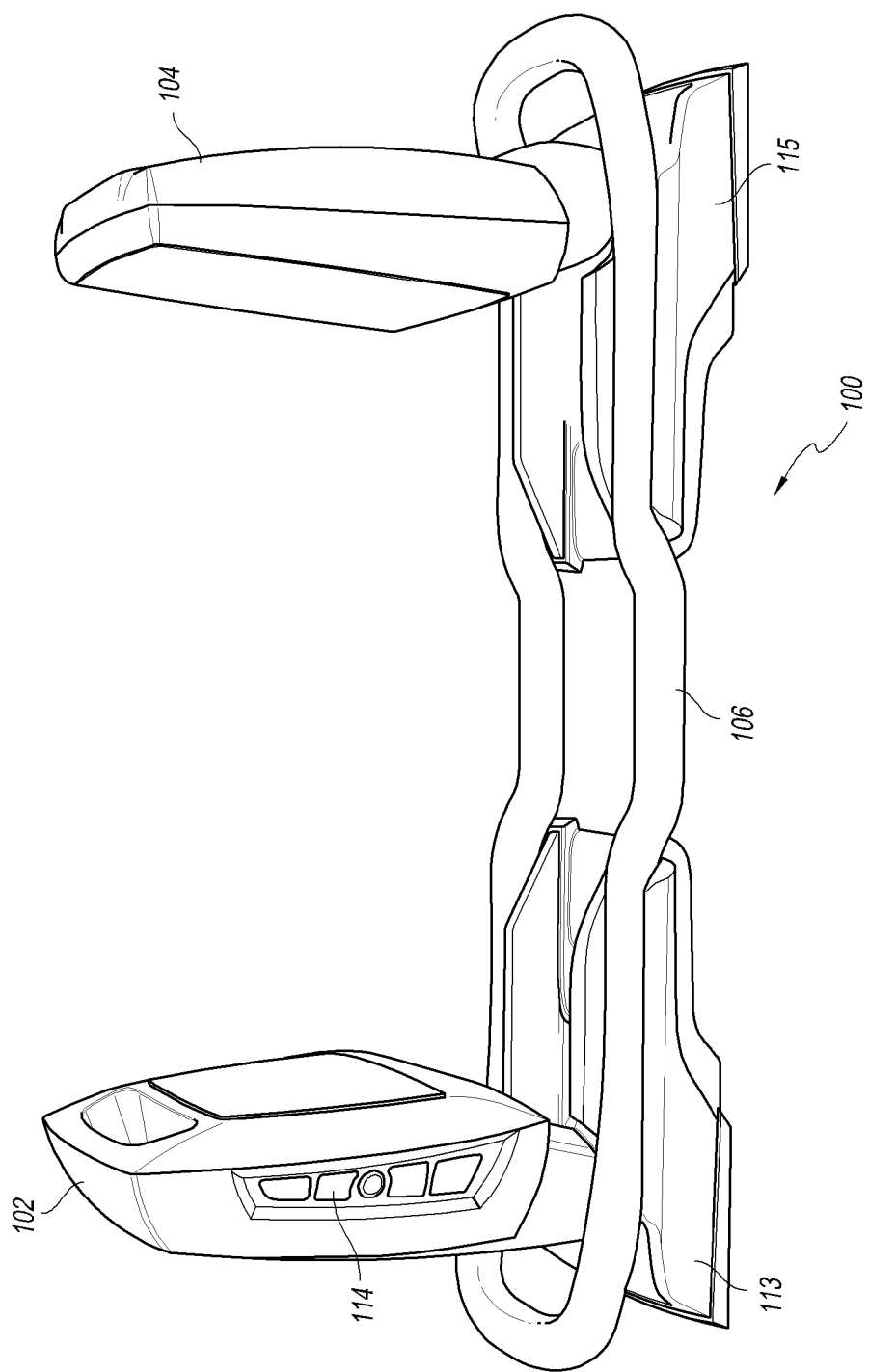
FIG. 2C illustrates a slightly angled view of the system of FIG. 2B, illustrating the connecting element as a looped bar that wraps circumferentially around the base members of both the respective x-ray source assembly and the image detection assembly.

FIG. 2C illustrates a slightly angled view of the system of FIG. 2B, illustrating the connecting element 106 as a looped bar that wraps circumferentially around the base members 113, 115 of both the respective x-ray source assembly 102 and the image detection assembly 104. In this embodiment, the base members 113, 115 rather than the connecting element 106 are in contact with a base surface (e.g., a table top or a floor) and provide stability for the device while on the base surface.

FIG. 3A illustrates the portability of the core mobile imaging system 100, that could include one or more wheels 116 attached either to the x-ray source assembly 102 or the detector assembly 104 portion of the system, or even attached to the connecting element 106. Wheels 116 allow the system 100 to be easily transported by rolling along the ground. The system 100 can also have one or more handles 112 as previously described. FIGS. 3B and 3C illustrates the core mobile imaging system 100 ready for imaging and having the longitudinal axis of the system 100 vertically and horizontally oriented, respectively.

Figure 4A:
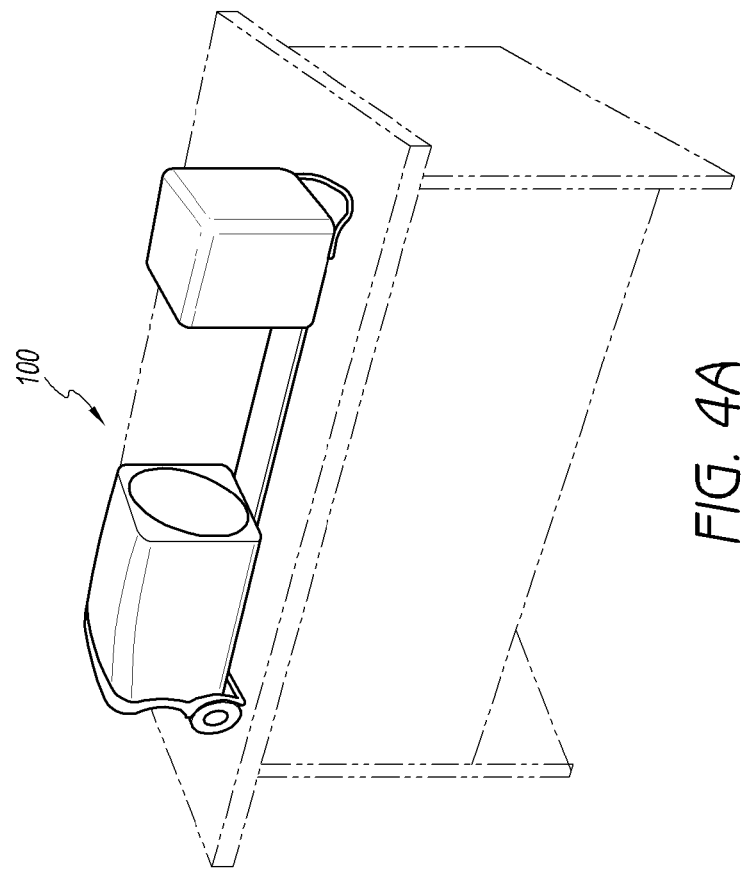
FIG. 4A illustrates a core mobile imaging system 100 conveniently positioned on a tabletop with the longitudinal axis of the system 100 oriented generally horizontally.
Figure 4B:
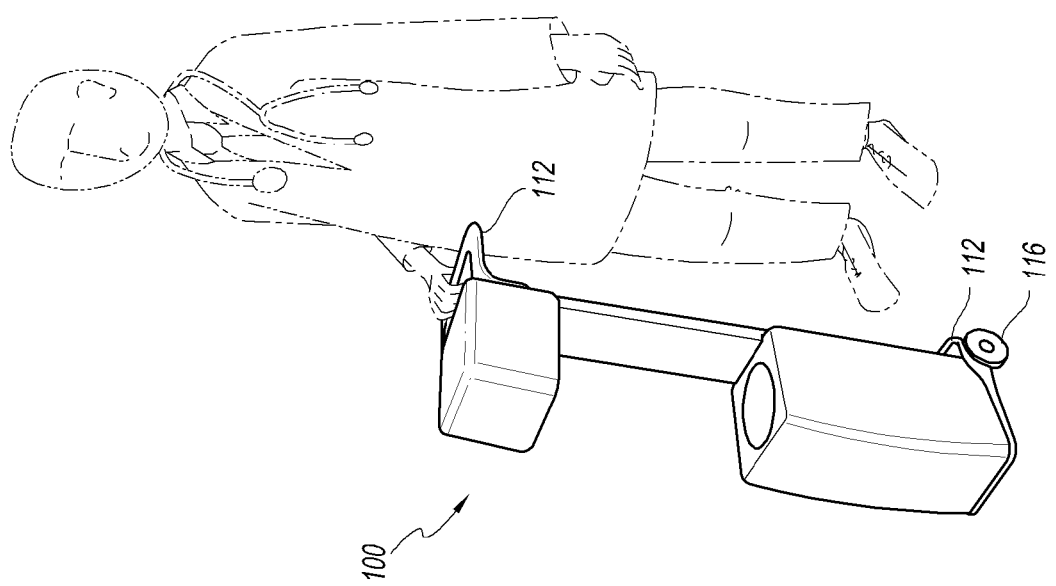
FIG. 4B illustrates a core mobile imaging system 100 being transported with its longitudinal axis oriented generally vertically.

FIG. 4A illustrates the core mobile imaging system 100 conveniently positioned on a tabletop with the longitudinal axis of the system 100 oriented horizontally. As previously noted, the imaging system 100 can also be positioned on either its left or right side, e.g., in lateral decubitus positions depending on the desired imaging position. The imaging system 100 can be light enough to be moved from the tabletop to the floor using handles 112, and then being rolled utilizing the wheels 116. FIG. 4B illustrates the core mobile imaging system 100 being transported with its longitudinal axis oriented generally vertically.

FIGS. 4C-4F illustrate handles 112, or grip points for use in lifting or moving the core mobile imaging system 100. As shown in the views of FIGS. 4C-4D, the handles 112 or grip points could be external and extend outwardly, or be internal, recessed in the x-ray source assembly, connecting element, and/or the detector assembly, as illustrated in FIGS. 4E-4F. In other embodiments, the handles 112 could be movable with respect to extend outwardly during use, but be retractable internally while not in use.

Figure 5C:
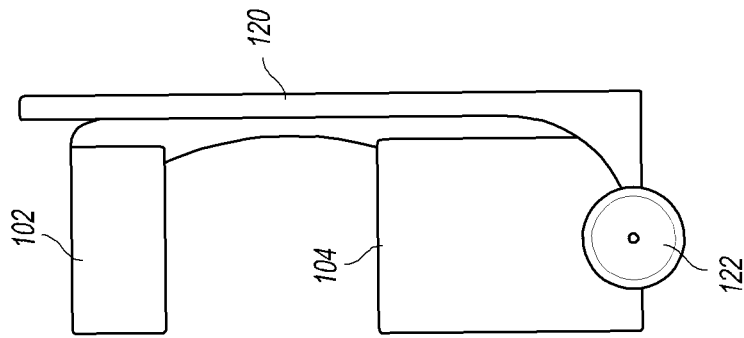
FIGS. 5A-5C illustrate that the core mobile imaging system can be removably attached to a stationary or movable cart that can have a base, wheels, and an elongate member that can be vertically oriented as illustrated.
Figure 5B:
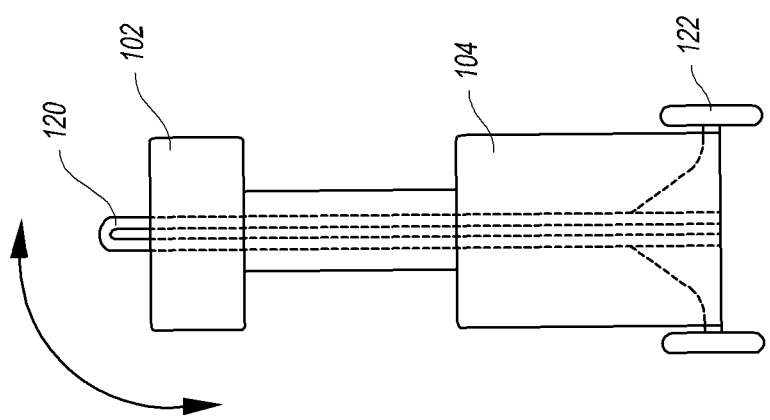
Figure 5A:
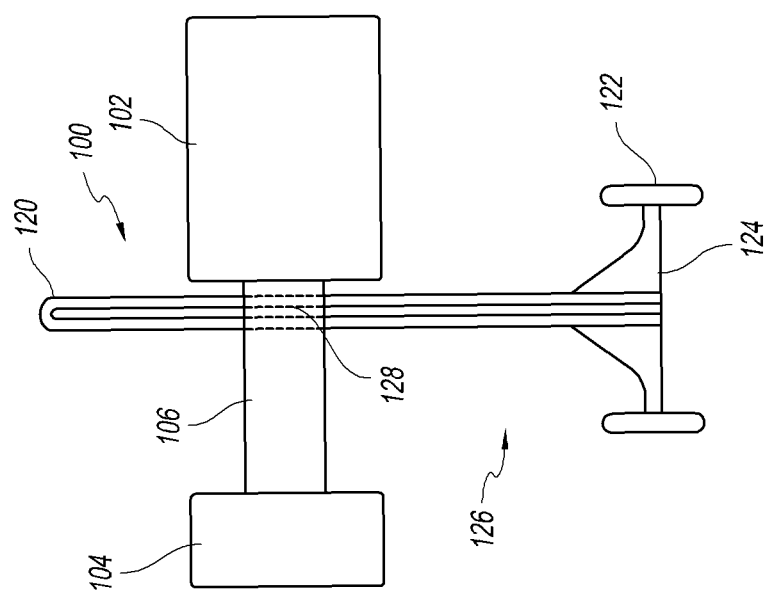

In some embodiments as shown in FIGS. 5A-5C, the core mobile imaging system 100 can be removably dockable via a coupler to a stationary or movable cart 126 that can have a base 124, wheels, 122, and an elongate member 120 that can be vertically oriented as illustrated. The cart 126 can include casters mounted into the base 124 to allow the cart 126 to balance various attached components. In some embodiments, one or more articulating joints 128 removably connects the connecting element 106 of the core mobile imaging system 100 with the elongate member 120 of the cart 126, to allow the imaging system 100 to have one, two, three, or more degrees of freedom with respect to the elongate member 120 of the cart 126. FIG. 5A illustrates the core mobile imaging system 100 with its longitudinal axis oriented horizontally, and attached to the elongate member 120 of the cart 126. FIG. 5B illustrates the core mobile imaging system 100 of FIG. 5A with its longitudinal axis oriented vertically, while FIG. 5C is a side view of FIG. 5B. In some embodiments, the elongate member 120 can have an axial length of between about 2 feet and about 8 feet, or between about 3 feet and about 6 feet.

FIGS. 6A-6C schematically illustrate non-limiting examples of possible degrees of freedom the core mobile imaging system 100 with respect to the elongate member 120 of the cart 126, according to some embodiments of the invention. As illustrated in FIG. 6A, the mobile imaging system 100 can move axially along the longitudinal axis A2 of the elongate member 120. As illustrated in FIG. 6B, the mobile imaging system 100 can rotate in a clockwise or counterclockwise direction in a plane that is parallel to the longitudinal axis A2 of the elongate member 120. Rotation could be limited to no more than about 30 degrees, 60 degrees, 120 degrees, 180 degrees, or 240 degrees, or the mobile imaging system could be configured to fully rotate 360 degrees. As illustrated in FIG. 6C, the mobile imaging system, 100 can rotate in a clockwise or counterclockwise direction around the longitudinal axis A2 of the elongate member 120. The system can include one, two, or more locking mechanisms to reversibly fix the core mobile imaging system 100 in a specified position.

Figure 7B:
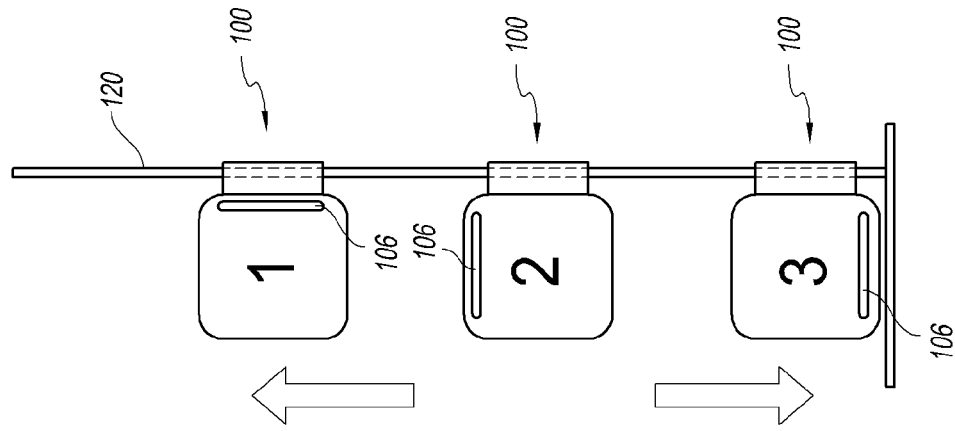
FIG. 7B illustrates in side profile three possible mounting configurations for the core mobile imaging system against a fixed vertically-oriented wall mount or elongate member.
Figure 7A:
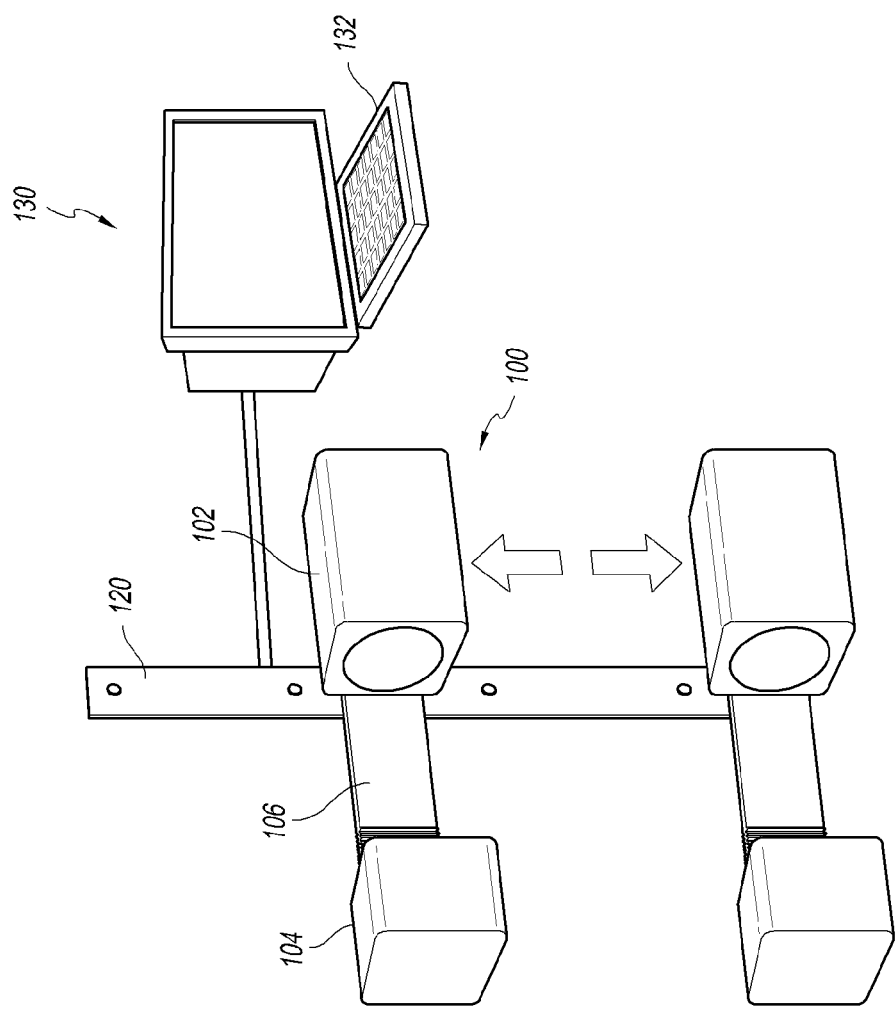
FIG. 7A illustrates a core mobile imaging system movable axially along the elongate member as described previously in FIG. 6A.

FIG. 7A illustrates a core mobile imaging system 100 movable axially along the elongate member 120 as described previously in FIG. 6A. Also illustrated is a display 130 with controls 132 (such as a keyboard or touchscreen on the display, for example) that can be connected via wires or wirelessly to the core mobile imaging system 100. A worm drive lift or similar mechanism allows for axial movement of the core mobile imaging system 100, for ease in imaging the appropriate anatomy of a patient. For example, being able to lower the imaging system 100 can allow for convenient imaging of a patient's foot or ankle without the patient having to lift his extremity off the ground. Being able to adjust the imaging system can allow for serial imaging of the cervical, thoracic, lumbar, and sacral spine, for example while the patient remains in the standing position. Furthermore, the one, two, three, or more degrees of freedom can allow for taking multiple images from different angles, increasing the sensitivity and specificity of diagnosis. FIG. 7B illustrates in side profile three possible mounting configurations for the core mobile imaging system 100 against a fixed vertically-oriented wall mount or elongate member 120 as previously described, with the connecting element 106 (also referred to herein as a deck) adjacent to the elongate member 120 or wall as in position (1); the connecting element 106 is in a relatively superior position as in position (2); and where the connecting element 106 is in a relatively inferior position as in position (3). The imaging system 100 can be easily attached and detached from the wall mount using clips, interlocking components, and the like.

Figure 8B:
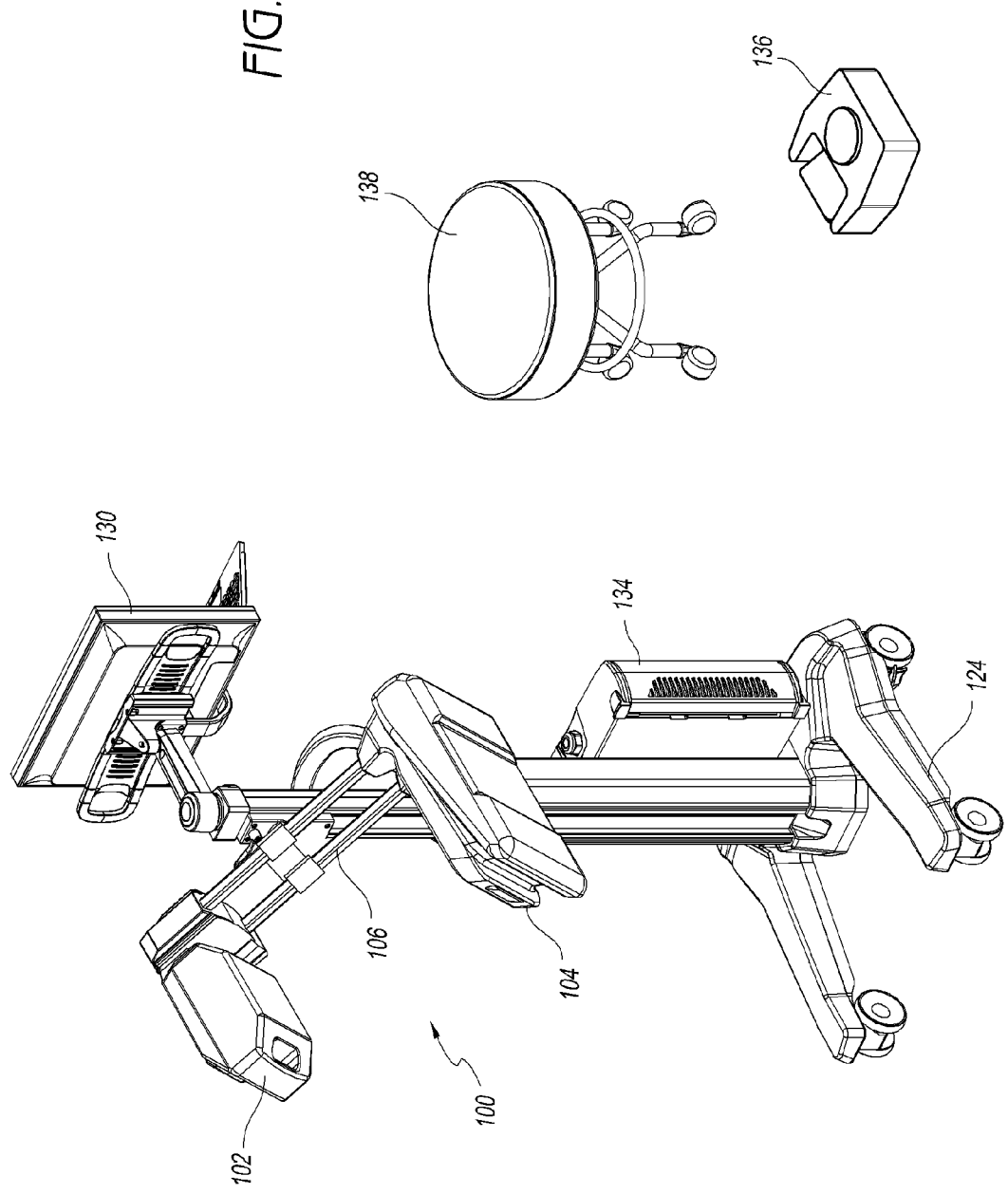
FIG. 8B illustrates an embodiment of a core mobile imaging system in an angled orientation and configured to rotate at least in a plane that is parallel to the longitudinal axis of the elongate member as previously described with respect to FIG. 6B.

FIG. 8A illustrates an embodiment of a core mobile imaging system 100 in a generally vertical orientation and attached to elongate member 120 of cart 126, similar to that described and illustrated in connection with FIG. 5B. Also shown is a display 130 connected to the elongate member 120, and computer 134 which can either be connected via wires or wirelessly to the core mobile imaging system 100 as previously noted. The system can also include external processing devices, printers, power supplies, cables, or other accessories related to the imaging system 100. FIG. 8B illustrates an embodiment of a core mobile imaging system in an angled orientation and configured to rotate at least in a plane that is parallel to the longitudinal axis A2 of the elongate member 120 as previously described with respect to FIG. 6B. Also illustrated is an operator stool 138 and a footswitch 136 with one, two, or more pedals connected with wires or wirelessly to the core mobile imaging system 100 and control one, two, or more functions of the core mobile imaging system 100, including activating and deactivating the x-ray source for imaging. The footswitch 136 could include membrane switches, momentary switches, or other actuation means.

FIGS. 9A-9C illustrate that the core mobile imaging system 100 can move from a first axially enlarged (open) configuration as illustrated in FIG. 9B during operation to a second axially reduced (closed) configuration in the direction of arrows of FIG. 9B, as illustrated in FIGS. 9A and 9C for convenient transport and/or storage. One or both of the x-ray source assembly 102 and the detector assembly 104 can be axially movable with respect to each other, such as on a track, slots, hinged mounting points, détentes, removable locking pins, or other means, and then carried using handles 112. In some embodiments, one or more of the components can be axially movable or rotatable along one, two, or more axes either manually or via an automated system, for example, using solenoids.

In some embodiments, the axial length of the core mobile imaging system 100 in its open configuration can be at least about 10%, 20%, 30%, 40%, 50%, or more greater than the axial length of the imaging system 100 in its closed configuration. The imaging system 100 can also have intermediate configurations where there remains a space between the x-ray source assembly 102 and the detector assembly 104, which can allow for a variable source to intensifier distance during operation, depending on the desired clinical result.

Figure 10:
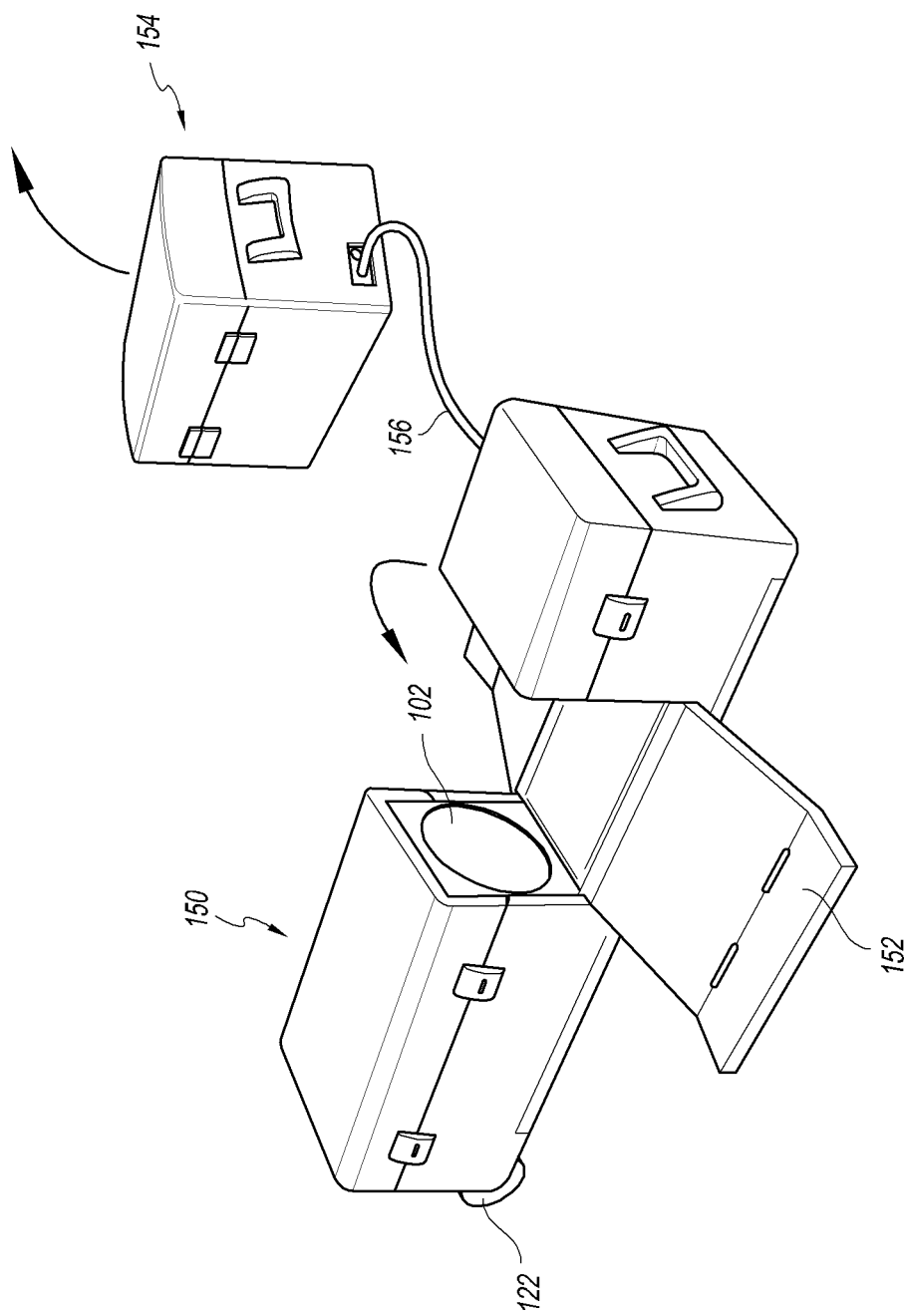
FIG. 10 illustrates a custom military-grade specification case for a core mobile imaging system, according to one embodiment of the invention.

FIG. 10 illustrates a custom military-grade specification case 150 for a core mobile imaging system 100, according to one embodiment of the invention. The case 150 is preferably rigid and can allow the imaging system 100 to be packaged, shipped and endure climatic or environmental duress for shipping or use in environments outside an air-conditioned controlled space. The case 150 can be envisioned in several different designs and form factors but would include such embodiments as a rugged outer shell that protects the device from vibration, shock, handling, electromagnetic radiation, moisture and other potential hazards. The case 150 could also serve as a platform upon which the imaging system 100 can be rested during use as a positioning aid, or to keep the imaging system 100 from coming into contact with various hazardous conditions that may exist on the ground at the point of use.

Case 150 can be shaped as a rectangular box corresponding to the form factor of the imaging system, or another desired shape, and include one, two, three, or more movable panels 152 to gain access to various components. For example, opening the panel 152 in between the x-ray source assembly and the detector assembly can be sufficient to image a desired anatomical structure. Case 150 may include wheels 122 for transport as previously described. In some embodiments, a wired (or wireless) conduit 156 connects the core mobile imaging system 100 to a second case 154 housing a display, CPU, or other components.

FIG. 11A illustrates another embodiment of a case 150 that may have a protective insert 158 that may be made of foam or similar material for the imaging system 100 shown in FIG. 11B and previously described. FIG. 11C illustrates the imaging system 100 within case 150 being rolled by a transporter using wheels 122 and handle 112.

Figure 12C:
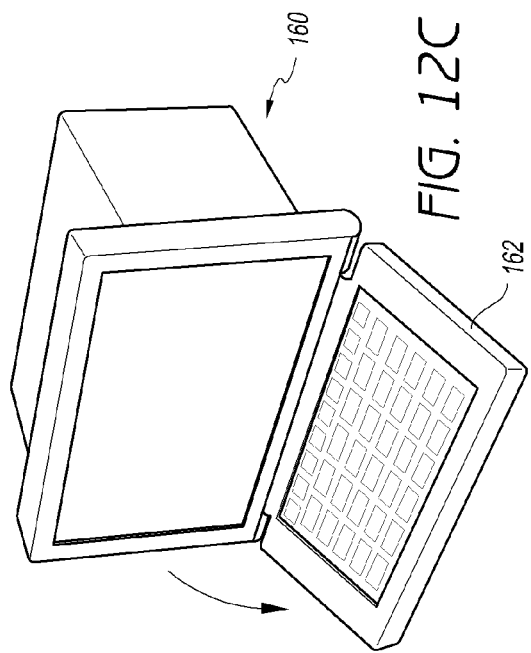
FIGS. 12A-12C illustrate a core mobile imaging system in which various accessory components can be nested within the imaging system for improved portability.
Figure 12A:
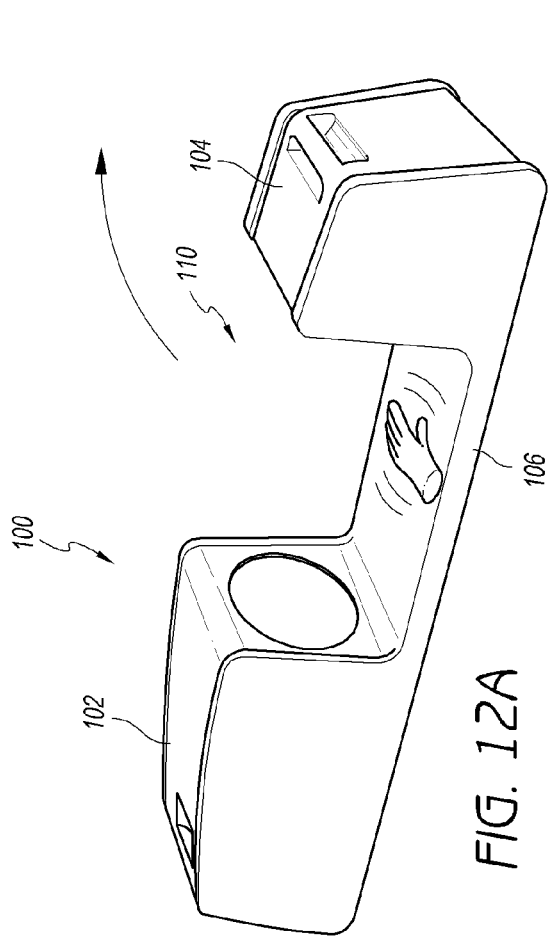
Figure 12B:
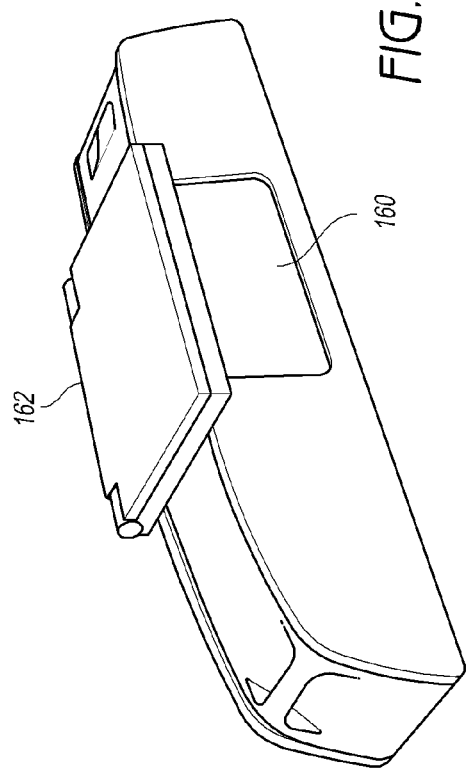

FIGS. 12A-12C illustrate a core mobile imaging system 100 in which various accessory components can be nested within the imaging system 100 for improved portability. Nested accessories could include, for example, a monitor, keyboard, control array or switch, processing device, printer, wireless communication accessory, and the like. For example, a display 160 and folding keyboard 162 can be nested within space 110 and thus stowed within the imaging system 100.

In some embodiments, the core mobile imaging system 100 comprises one, two, or more wireless terminals that can display images, control functions of the core mobile imaging system, or both. Traditional x-ray devices such as plate x-ray systems, dental x-ray systems, digital radiographic systems, and fluoroscopic x-ray systems have included displays and/or controls discrete from, but still hard-wired or tethered to, the imaging component to provide increased measures of safety and convenience for the operator. However, these controls were limited to a predetermined location or useful range as the monitor for the data was fixed in one or several locations. When wireless controls were provided, they were limited in function and did not combine and/or include the video signal required to monitor the device. While PACS servers and viewing stations have increased the flexibility of viewing options, they do not allow the user to combine real-time control and monitoring of the x-ray data from a single portable (untethered) monitoring station. The operation of an x-ray device is usually controlled by a single control station, or a number of fixed control stations that are either physically connected to the device itself, or positioned at one or more predetermined locations for reasons of safety or convenience. The use of a combination wireless video image viewer/monitor and control system will allow a user to advantageously watch real time data and/or review previous data and control the functions/parameters of the x-ray producing device with the same remote device from any number of locations within the recommended wireless communication distance, allowing a larger degree of occupational safety, versatility in the use of the device, and greater flexibility in positioning the x-ray subject. The ability of the core mobile imaging system 100 to interface, such as wirelessly with various monitor devices allows the core mobile imaging system 100 to be transported from a first location to a second location without the burden of a large, heavy, and/or bulky monitor device physically attached. The core mobile imaging system 100 is advantageously configured to interface with a wireless combination image viewer and function control device that can be transported separately from the core mobile imaging system itself, further increasing the portability of the system.

In some embodiments, the core mobile imaging system 100 is configured to broadcast the video signal (which includes, but is not limited to static x-ray image data, dynamic fluoroscopic x-ray imaging data, e.g., between about 3 frames per second and about 70 frames per second, or between about 15 frames per second and about 60 frames per second) from a video processor on the core mobile imaging system 100 via a wireless communication protocol to one, two, or more devices that will process, transmit, retransmit and/or display the video signal. The core mobile imaging system 100 will be able to transmit this signal to a standard or high-definition television, medical grade monitor, tablet computer, laptop computer, desktop computer, smartphone, wireless device, network interface, network hub, and/or other device(s) capable of receiving, broadcasting, and/or displaying this signal. This signal could be a standard or non-standard protocol such as, for example, 802.11x, 802.16x, Bluetooth, FireWire, Wibree, ZigBee, Wireless USB, UWB, VEmesh, EnOcean, CDMA, UMTS, LTE, or any other protocol listed herein.

Figure 13A:
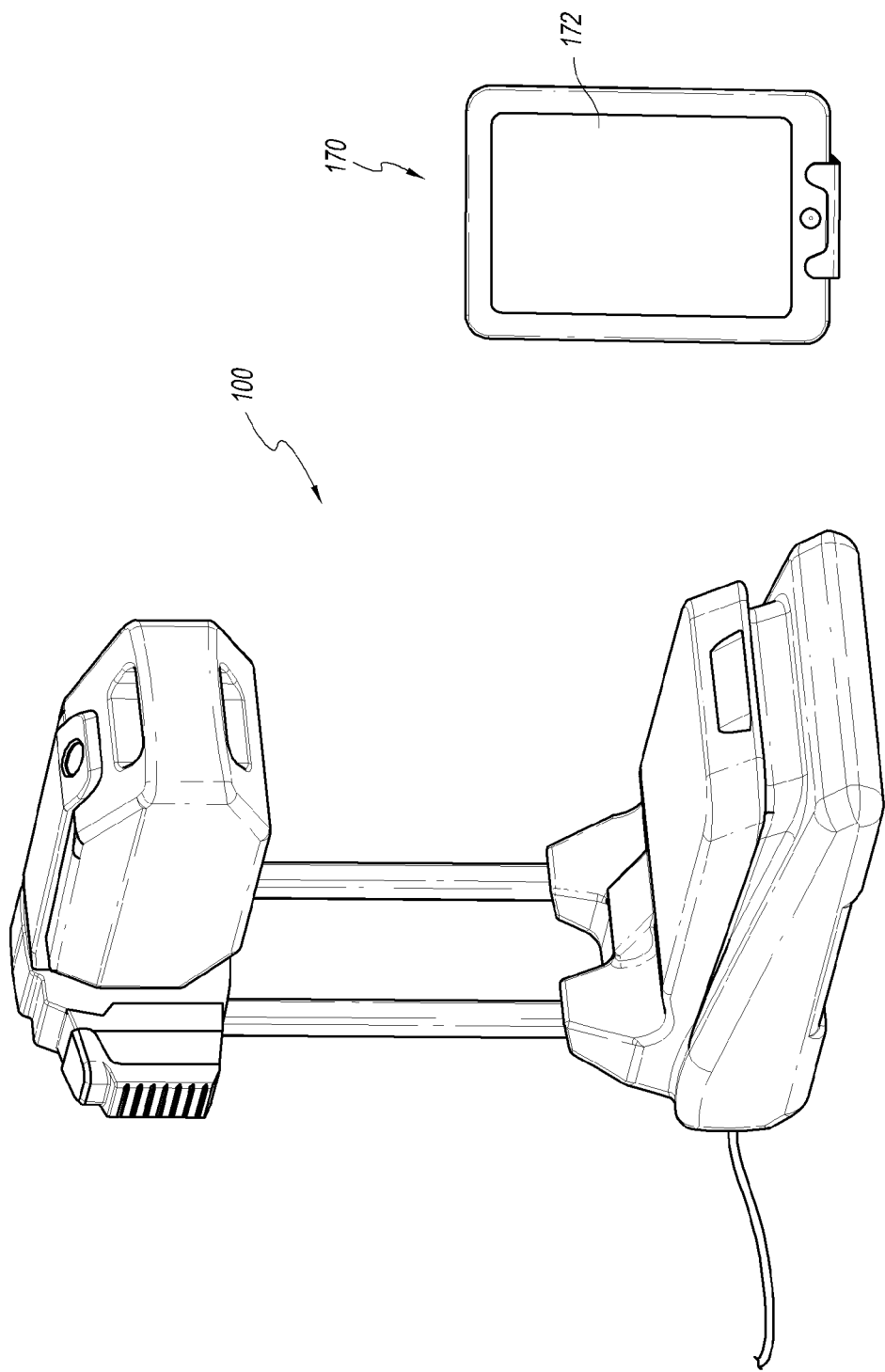
FIG. 13A illustrates a core mobile imaging system and a wireless remote viewer/control.

In addition to sending imaging data wirelessly, the core mobile imaging system 100 can also be configured to communicate wirelessly (such as to a combination image viewer/remote control system) via hardware and/or software to allow a user remote, untethered input of data and commands to the system, as well as data monitoring, system configuration and control of system functions. Examples of such interactions would include but not limited to, data input, system configuration input, system settings input, system control input, notification of functions or events, initiation of functions or events, and the like. FIG. 13A illustrates a core mobile imaging system 100 and a wireless remote viewer/control 170. The wireless remote viewer/control could have a touchscreen 172 (or a screen that does not respond to touch controls), one, two, or more physical controls, or a combination thereof. While illustrated for clarity in relatively close proximity to each other, it will be understood that the wireless remote viewer/control 170 could be located in a location further remote from the core mobile imaging system, such as at least about 10 feet, 25 feet, 50 feet, 100 feet, 200 feet, 500 feet, 1000 feet, a mile, or more; or in a different room, a different floor, a different building, or even a different city.

In some embodiments, the core mobile imaging system 100 is motorized such that it is configured to move in response to a command provided by a wireless remote control system.

For example, the system 100 can include position sensors, e.g., a global positioning system chip, camera, accelerometer, and/or gyroscope, such that a remote user can track the system 100 and/or remotely determine the position of, or order the system (such as one having wheels) to move in a desired direction, such as forward, in reverse, laterally, or to rotate; adjust the axial distance between the x-ray source assembly and the detector assembly; and/or to move or rotate an connecting element operably connected to an elongate member of a cart illustrated in FIGS. 6A-7A for example.

Power systems for x-ray producing devices are typically built into the large cabinets associated with the x-ray device. In large digital radiographic systems, the generators require large capacitive loads to operate and as such require large cabinets to house the electronics that are typically floor or wall mounted with a specified receptacle and associated electronic infrastructure to supply the unit. Mobile fluoroscopes that move room to room in the same way house the power electronics within the large mobile cabinet(s) to allow convenient transport. For conventional miniature fluoroscopes (miniature C-arms) the power electronics are built into the main cabinet of the system for ease of use and transport.

In a mobile application for an x-ray device in which the physical size of the cabinet housing the x-ray device is a design constraint, the power electronics could be housed in an external compact enclosure separated from and spaced apart from the core mobile imaging system 100 itself, ruggedized and having a minimized footprint. This discrete compact power electronics unit would allow for the core mobile imaging system 100 to be lighter in weight, more compact in form factor, and allow multiple, more flexible transport configurations by nesting the external power unit within the volume of the x-ray device. In a similar manner in which the transformer and AC or DC power circuits for a laptop computer are decoupled from the body of the laptop computer itself in an external power unit, such an external power unit would provide advantages in weight, configuration versatility, transportation versatility, serviceability and form factor for a core mobile imaging system.

Figure 13B:
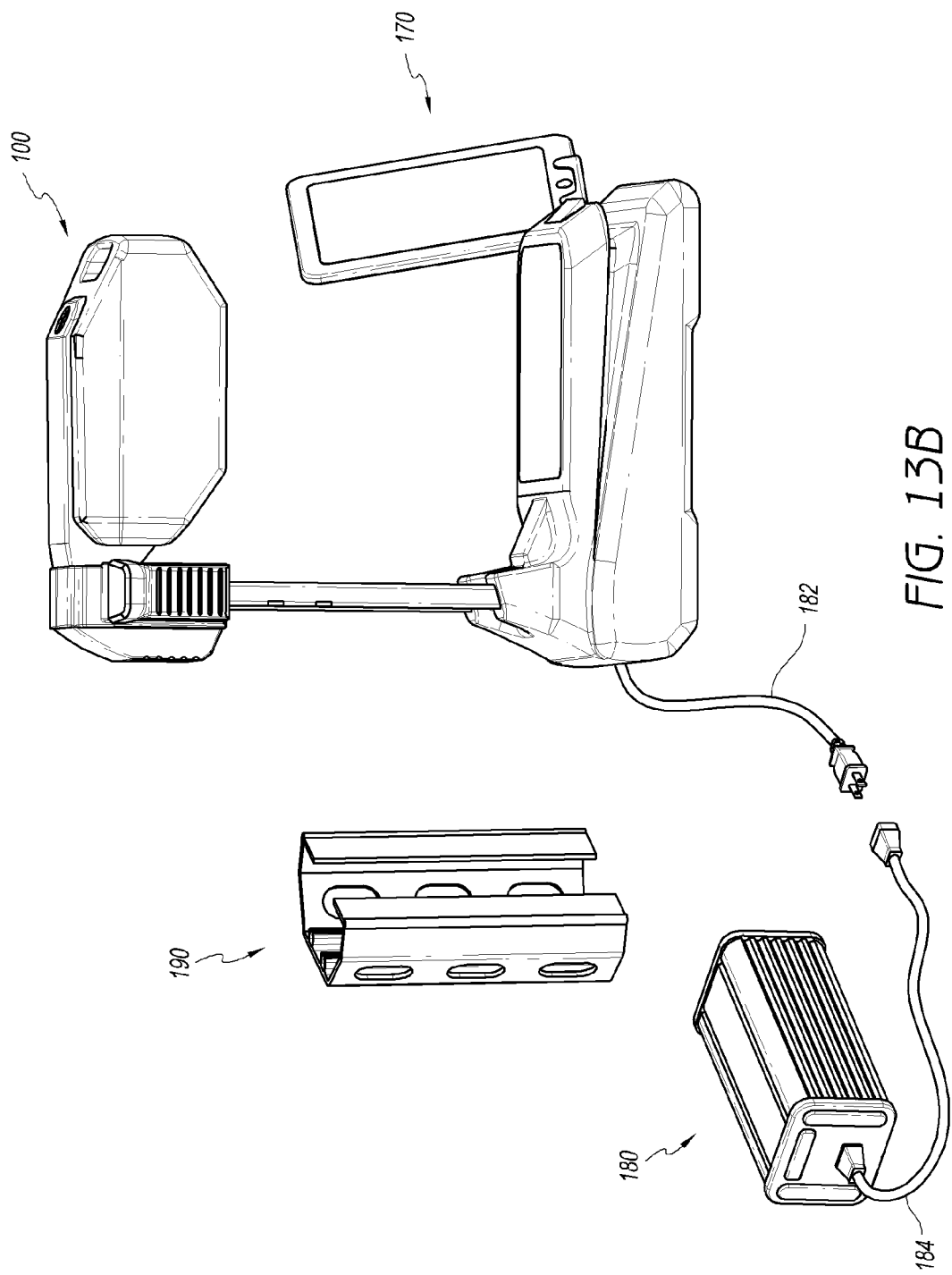
FIG. 13B illustrates an embodiment of a core mobile imaging system, along with accessory components including wireless remote viewer/control, external power unit, and foot-positioning accessory.

FIG. 13B illustrates an embodiment of a core mobile imaging system 100 and wireless remote viewer/control 170 as previously described. Also illustrated is an external power unit 180 that is permanently or removably attached via first power conduit 182 to the core mobile imaging system 100. Power element 180 could be a direct source of power such as a battery that can be charged by second power conduit 184, or alternatively a power adapter connected via second power conduit 184 to another discrete power source. Also illustrated is a foot positioning accessory 190 that will be described in greater detail infra. In still other embodiments, the core mobile imaging system 100 could be charged wirelessly via an inductive charging device.

FIG. 13C illustrates one possible embodiment of a transport or storage configuration for a core mobile imaging system 100, with the wireless remote viewer/control 170 and external power unit 180 stored in the space 110 in between the x-ray source assembly 102 and the detector assembly 104. The foot positioning accessory 190 could be also stored within in the space 110, or alternatively partially enveloping the connecting element 106 as illustrated.

The core mobile imaging system 100 could be designed to operate on a number of direct current voltages. These direct current voltage supplies could be supplied via connected cable by the external power unit 180 that can house a power transformer to both step down input voltage and provide line isolation in-line with several channels of discrete component electronics in combination to output/provide several distinct DC voltages as appropriate for operation. The external power unit 180 could be plugged into/supplied by either an alternating current power supply (e.g., 120V or 240V) such as a wall receptacle or generator receptacle, or alternatively to a direct current source such as a battery or other capacitive generator. In the case of the direct current supply source, the external power unit 180 could either be physically affixed to the DC capacitive generator or be connected via cable. Use of an external power unit 180 can advantageously allow for a lighter in weight, more compact core mobile imaging system 100. It will also provide for greater serviceability in that the external power unit 180 can be replaced or repaired without disturbing or opening the sensitive electronics associated with the x-ray generating components of the core mobile imaging system 100. The compact but separate enclosure would provide for a wider variety of transportation and operation configurations. In some embodiments, the external power unit is no more than about 12 inches in length, no more than about 8 inches in width, and/or no more than about 8 inches in height.

Figure 13D:
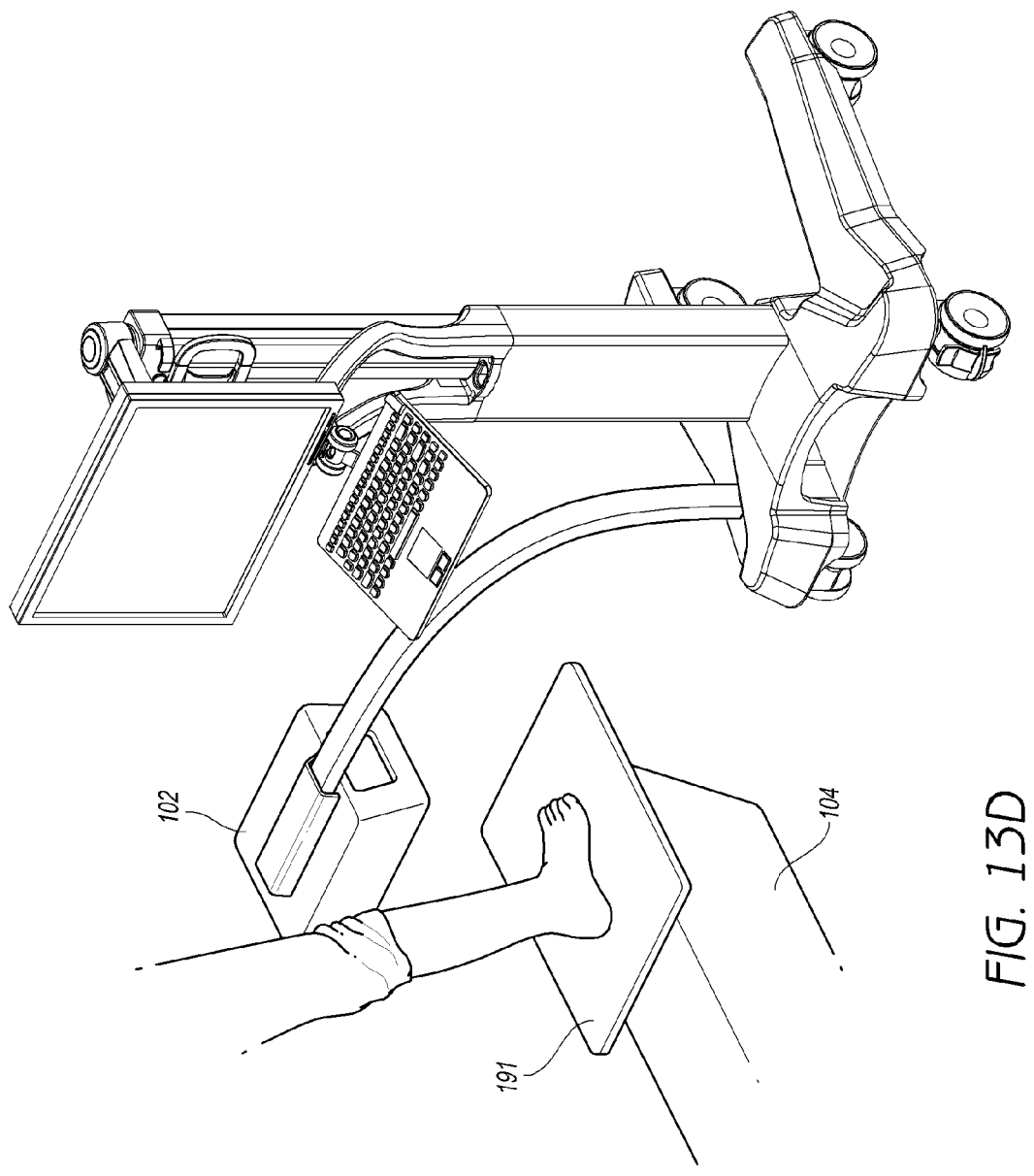
FIG. 13D illustrates a plank developed for a C-arm type imaging system.

In order to acquire load-bearing views of certain anatomical structures, e.g., a foot, an x-ray device should allow a patient an area to stand under which, and lateral to which, an image receptor or x-ray source is positioned, depending on whether the desired view is Posterior-Anterior (PA), Anterior-Posterior (AP), oblique, or lateral for example. However, with respect to these image views using mobile or portable fluoroscopy technology, the view in which the image receptor assembly 104 is positioned below the foot has been very limited by the use of image intensifier-type image receptors which have a considerable height or vertical dimension. As an example, when positioning an image-intensified fluoroscope underneath a foot for an AP view of the metatarsals, the weight of the patient is supported either above the image intensifier, or occasionally on top of the image receptor/intensifier itself. This requires the patient to step up and overcome the vertical height of the intensifier, typically in excess of 14 inches (35 cm), which may be challenging and create a risk of the patient falling off the device, especially given a patient with a foot injury. This has typically limited the utility of such a device to obtain the view, which has often required the use of a "diving board" or plank 191 positioned several feet vertically about the ground developed for a much larger C-arm type imaging system between the x-ray source assembly 102 and the receptor assembly 104, and just superior to the receptor assembly 104 on which the patient stands on, as illustrated in FIG. 13D (such as one developed by Dr. Michael Graham). With the use of a flat detector in a fluoroscope, the overall height of the component placed under the foot can be much smaller (typically less than about 6 inches (15 cm)) allowing the user to either stand directly on the detector assembly 104 housing for the view, or utilizing a much smaller, shorter and more transportable accessory for positioning the patient's foot to be imaged over the detector assembly 104. This anatomy-positioning accessory, such as a foot-positioning accessory, could allow for positioning of the patient and the x-ray imaging device to obtain the load-bearing or standing foot views (e.g., AP, PA, lateral, and/or oblique views). This foot-positioning accessory could also be compact, and capable of nesting within the physical volume of the x-ray imaging device when not in use, or attached to the core mobile imaging system 100 in various combinations to provide desired x-ray views when the imaging system is in use. While described herein primarily as a foot-positioning accessory, the accessory could also be utilized to rest other anatomical structures to be imaged, such as a hand or arm for example, which could be advantageous in a patient who is comatose or otherwise altered, sedated, demented, or otherwise has weakness or paralysis such that they are unable to keep the anatomical structure to be imaged suspended in the air between the x-ray source assembly and the detector assembly sufficient to take the desired imaging.

Figure 13E:
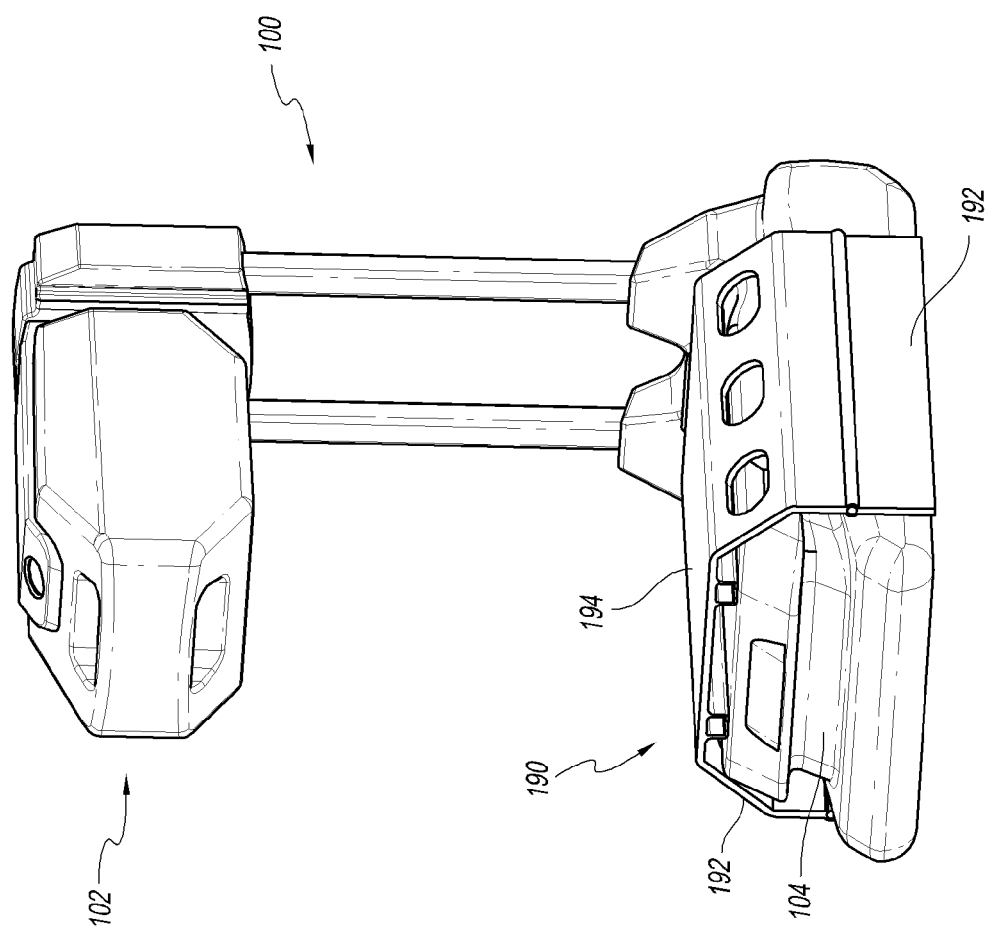
FIG. 13E illustrates an anatomical-positioning assembly, such as a foot-positioning accessory for the core mobile imaging system to facilitate common imaging views associated with x-ray positioning of the foot.
Figure 13F:
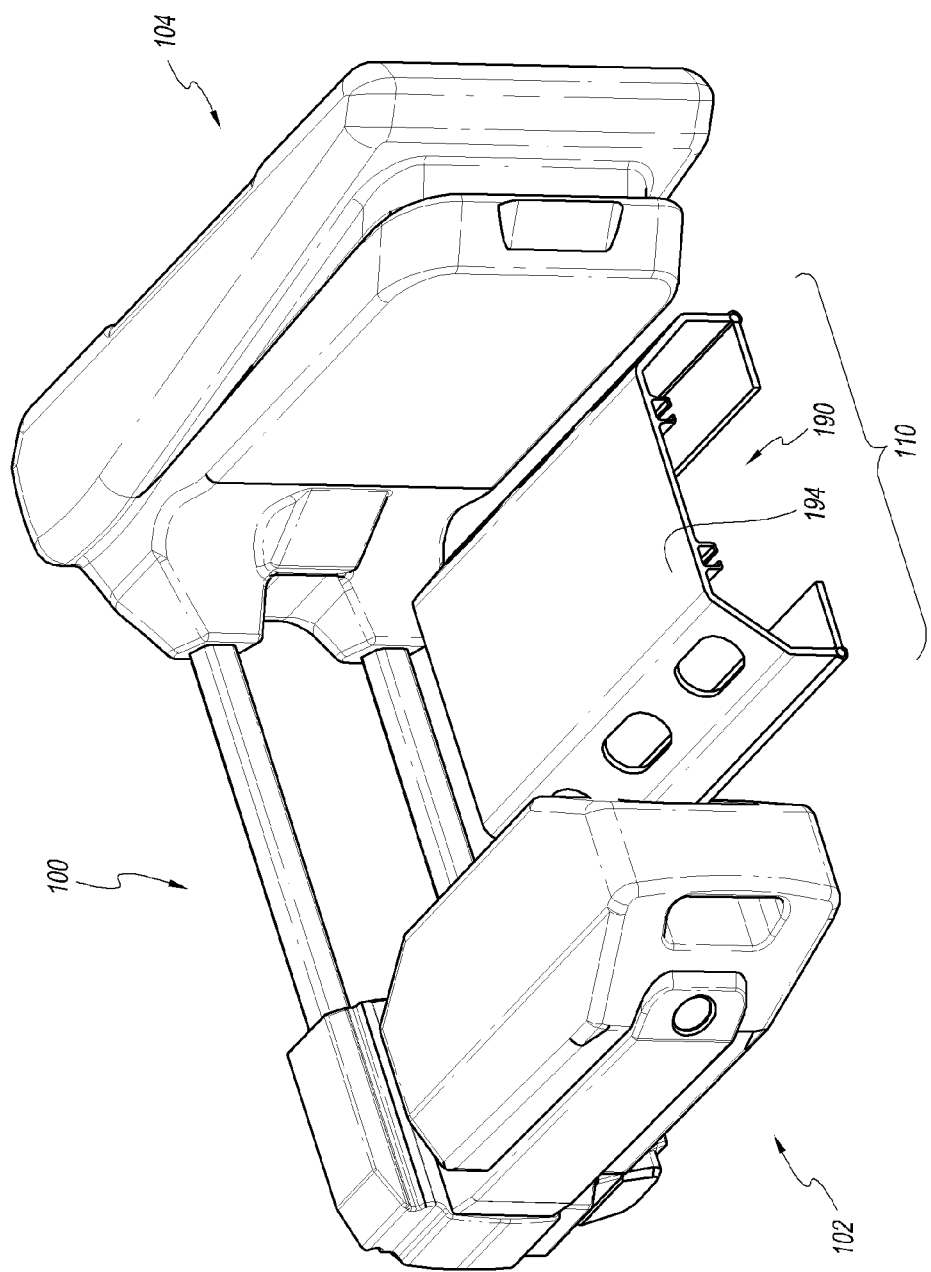
FIG. 13F illustrates an embodiment of a foot positioning accessory (where the patient can position their foot positioned in the space in between the x-ray source assembly and the detector assembly while the core mobile imaging system is in a relatively horizontal orientation.

FIG. 13E illustrates an anatomical-positioning assembly, such as a foot-positioning accessory 190 for the core mobile imaging system 100 to facilitate common imaging views associated with x-ray positioning of the foot. These views would include but are not limited to AP, PA, lateral, and oblique views of the foot and ankle. The foot-positioning accessory 190 would also allow these projections to be made in relaxed or non-load bearing or stressed views as well as load-bearing or weighted views or stressed views. The foot-positioning accessory 190 includes a relatively horizontally-oriented central portion 194, which could have a square, rectangular, circular, oval, or other desired surface geometry in some embodiments, for the patient to place their foot upon. The foot-positioning accessory 190 could also optionally relatively vertically-oriented, angled, or curved side walls 192 for connecting and distributing forces from the central portion 194 of the foot-positioning accessory 190 to the ground. In some embodiments, the foot-positioning accessory 190 could be transformed into a smaller footprint configuration for storage or transport. For example, hinges could be present between the central portion 194 and the side walls 192 allowing the side walls 192 to fold onto the central portion 194. At least the central portion 194 of the foot-positioning accessory 190 made be constructed, for example, of a radiotransparent or relatively radiotransparent material that does not interfere with imaging of the anatomical structure to be imaged. FIG. 13F illustrates an embodiment of a foot positioning accessory 190 (where the patient can position their foot positioned in the space 110 in between the x-ray source assembly 102 and the detector assembly 104 while the core mobile imaging system 100 is in a relatively horizontal orientation. In other words, the longitudinal axis of the core mobile imaging system 100 is aligned relatively horizontally, which is parallel to, or coaxial with a relatively horizontal axis of the central portion 194 of the foot-positioning accessory 190. The relative orientation of the foot-positioning accessory 190 with respect to the core mobile imaging system 100 shown in FIG. 13F can be especially advantageous when, for example, taking lateral views of a foot or ankle.

In some embodiments, a relatively short height of the foot positioning accessory 190, e.g., under about 24 inches, 18 inches, 15 inches, 12 inches, 10 inches, or less in height on which the patient would stand for load bearing views can be accommodated by using a flat detector image receptor rather than an image intensified image receptor. In some embodiments, the foot-positioning accessory 190 has a maximum length dimension of no more than about 4 feet, 3.5 feet, 3 feet, 2.5 feet, 2 feet, 1.5 feet, 1 foot, or less and/or a maximum width dimension of no more than about 4 feet, 3.5 feet, 3 feet, 2.5 feet, 2 feet, 1.5 feet, 1 foot, or less. This relatively lower height provides for a safer examination for the patient and operator and an easier pose for the patient as they are not required to climb several feet above the ground as with the embodiment illustrated in FIG. 13D. The foot-positioning accessory 190 would either be directly attached or detached and separate from the core mobile imaging system 100 depending on the view and stability required for the desired imaging view.

Typical uses of mobile c-arm fluoroscopes and miniature c-arm fluoroscopes in particular are limited by their mobile cabinets bulk and overall weight (typically over 400 lbs. (181kg)). Many operating theaters and examination rooms have limited space for surgical operation, personnel and equipment, and this space is typically a budgeted commodity when space planning and operating. Attaching and positioning a fluoroscope within this surgical environment or examination room in a manner that minimizes the impact on footprint, volume and weight with the objective of improving workflow and available space creates a distinct advantage for an imaging device. Creating a core mobile imaging system with a suitably light mass, e.g., less than about 100, 80, 60, 50, 40, 30 or less pounds, and small overall footprint would allow for mounting the device on a number of positioning aids to accommodate these goals of reduced footprint or space requirement. Three non-limiting such means of accomplishing this would be to design the x-ray device in such a way as to have common mounting hardware points to attach or affix to several different mounting accessories such as a counterbalanced ceiling mounted surgical positioning arm, or wall mounted static positioned bracket or mobile cart with a footprint smaller than currently available comparable imaging modalities.

Figure 13G:
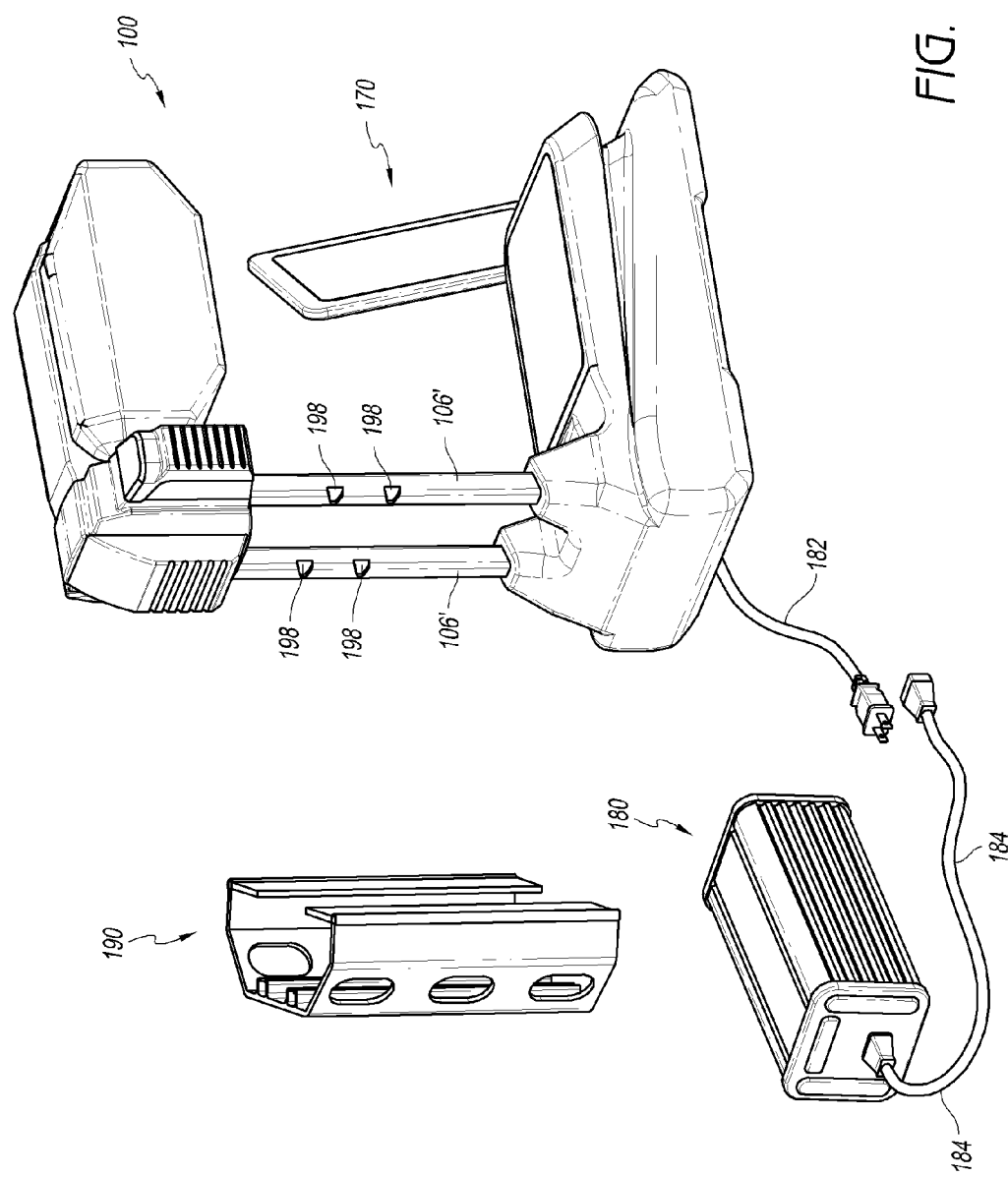
As illustrated in FIG. 13G, the core mobile imaging system can be provided with predetermined mounting hardware receptacle that would allow the core mobile imaging system to be attached or affixed to a number of accessory or positioning devices.

As illustrated in FIG. 13G, the core mobile imaging system 100 can be provided with predetermined mounting hardware receptacle(s) 198, which could include but is not limited to apertures, a post pattern, a mounting plate, a mounting vice, hooks, detents or other means of permanent and temporary mechanical fastening that would allow the core mobile imaging system to be attached or affixed to a number of accessory or positioning devices. As illustrated in the example of FIG. 13G, there are four apertures cut into metal bars, two each on each elongate bar 106' of the connecting element 106 of the system 100 to allow mechanical fastening to various accessories. The means by which the device is fastened to these accessories can be standardized or utilize an adapter to mount to existing devices such as surgical theater ceiling-mounted arm booms. The accessory positioning devices can optionally provide power, video process cabling or other input/output functions in combination with mechanical positioning. The positioning aids would allow the unit to be pulled into the proximity of a surgical operation or examination procedure and then moved out of the field of operation or examination in such a way as to not require any floor space when not in use. Current trauma bays utilize ceiling or floor mounted fluoroscopes in a similar way, but the fluoroscope is not readily or easily transportable from room to room or facility to facility due to the large weight, volume and electrical design. Utilizing a portable or mobile device such as a self-contained x-ray fluoroscope that can attach, detach and reattach to a common mounting hardware solution, but be moved from room to room or location to location would provide an advantage in versatility and mobility of such a solution and be able to be removed from the room when not in use, or utilized in a different room or facility as desired by the operator.

The systems described above could be useful for a wide range of diagnostic and therapeutic applications. For example, the systems could be used when real-time observation of a suspected fracture under stress or motion could confirm a fracture. Using the real-time imaging capacity of imaging systems as described herein, a physician can obtain a first diagnostic screening opinion without having to wait for films to be developed. The systems described above can also assist during open and closed reduction of fractures. In closed reduction, fracture fragments are aligned without surgery (e.g., by applying traction). The use of a mobile imaging system as described above can be particularly useful during external fixation because it allows bone fragment alignment to be viewed noninvasively in real time. In open reduction, surgery is performed to reduce the fracture, and internal fixation devices, such as pins, screws, plates, and intermedullary rods, may be used. The mobile imaging system can allow correct insertion of the fixation devices to be monitored fluoroscopically. This procedure allows quick visualization of, for example, whether the pin has actually traversed the bone completely and is resting in soft tissue. If incorrect placement of the fixation devices is noted, it can then be immediately corrected.

Injuries resulting from a retained foreign body (typically wood, metal, or glass) in an extremity such as the hand or foot are very common. The standard procedure in such injuries is first to identify the location of the foreign body using radiographic films and then to remove the object. When necessary, fluoroscopic visualization can help with the removal. The ability to visualize the foreign body from various projections, as is possible with mobile imaging units as described herein, is especially useful in that it enables the image of the foreign body to be cast away from underlying bone. Metal and glass fragments are easily visualized on x-ray images.

Mobile imaging systems as described herein could be particularly useful for assessing joint conditions because x-ray images of the joint can be obtained in real time and from a variety of different projections as the joint is exercised. Joint disorders are often clearly detectable on motion of the joint. One example would be when a patient has painful clicking or popping that accompanies a certain motion; the joint can be visualized in real time during this motion to diagnose the cause of the pain. With fluoroscopy, real-time visualization of a contrast medium as it flows through a joint is also possible. Because the typical joint is a collection of different bones held together by cartilage and ligaments, contrast flow studies often help to show cartilage and ligament tears, as well as bone fractures. Arthrography (contrast-enhanced joint studies) has been shown to be efficacious in detecting wrist, elbow, and knee abnormalities.

Fluoroscopy, particularly angiography, has proven to be useful in detecting vascular abnormalities. Angiography is often performed to assess the severity of extremity trauma wounds (e.g., gunshot wounds) and to study congenital and acquired vascular malformations in the hands and feet. It is also used to show vascular structure when transplant surgery is being considered. Fluoroscopic procedures could be used with the imaging systems as described herein.

Bone spurs—bony tissue growths that often cause severe pain—occur fairly commonly in the feet; typically, they can be well identified on radiographs. However, fluoroscopy is especially useful in assessing the course of surgical intervention. Fluoroscopically guided bone biopsies and cyst aspirations can be readily accomplished because fluoroscopic imaging can easily demonstrate the location of a metallic needle in tissue and allows real-time imaging. Bone biopsies may be indicated for suspected bone neoplasms or for assessment of the severity of osteoporosis. Cyst aspirations are often necessary as a result of infectious conditions in which fluid collects in a specific region of the body. The aforementioned imaging systems can be utilized to perform the above.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

I claim:

1. A portable, imaging system, comprising:
a support having a connector;
an x-ray source carried by the support;
an x-ray detector carried by the support and positionable at a distance from the source;
a primary x-ray propagation axis extending between the source and the detector;
a first surface on an opposite side of the source from the detector;
a second surface on an opposite side of the detector from the source;
at least a third surface generally parallel to the axis, wherein the system can be free-standing on each of the first surface such that the axis extends generally vertically, the second surface such that the axis extends generally vertically, and the third surface such that the axis extends generally horizontally, and wherein the system is configured to take images using the x-ray source and the x-ray detector when placed on a horizontal surface on either of the first or second surfaces such that the axis extends generally vertically, or on the third surface such that the axis extends generally horizontally; and
an elongate member having an axis, wherein the elongate member is configured to detach and reattach the connector and allow movement of the support, x-ray source, and x-ray detector in at least one degree of freedom with respect to the elongate member axis.

2. An imaging system as in claim 1, wherein the distance along the x-ray propagation axis between the source and the detector is adjustable.

3. An imaging system as in claim 1, wherein the detector is a flat detector.

4. An imaging system as in claim 1, further comprising a monitor.

5. An imaging system as in claim 4, wherein the monitor is wirelessly connectable to the detector.

6. An imaging system as in claim 1, further comprising at least a first control panel on the source, and at least a second control panel on at least one of the detector and the support.

7. An imaging system as in claim 1, wherein the source is configured to produce a pulsed x-ray beam.

8. An imaging system as in claim 1, wherein the elongate member is a track vertically fixed to a portable cart.

9. An imaging system as in claim 8, further comprising a mechanism configured to mechanically move the connector with respect to the track.

10. An imaging system as in claim 1, wherein reversible attachment of the connector to the elongate member allows linear translation of the support, x-ray source, and x-ray detector along the elongate member axis.

11. An imaging system as in claim. 1, wherein reversible attachment of the connector to the elongate member allows rotation of the support, x-ray source, and x-ray detector in a plane substantially parallel to the elongate member axis.

12. An imaging system as in claim 1, wherein reversible attachment of the connector to the elongate member allows rotation of the support, x-ray source, and x-ray detector in a plane substantially perpendicular to the elongate member axis.

13. An imaging system as in claim 1, further comprising at least one locking element configured to reversibly fix the connector and support in a specified position with respect to the elongate member.

\* \* \* \* \*

UNITED STATES PATENT AND TRADEMARK OFFICE
CERTIFICATE OF CORRECTION

| | | |
|---|---|---|
| PATENT NO. | : 9,125,611 B2 | Page 1 of 1 |
| APPLICATION NO. | : 13/324677 | |
| DATED | : September 8, 2015 | |
| INVENTOR(S) | : Christopher B. Eaves | |

It is certified that error appears in the above-identified patent and that said Letters Patent is hereby corrected as shown below:

In the Specification

In column 1 at line 9 (approx.), Change "Feb. 28, 2011," to --Jan. 31, 2011,--.

In the Claims

In column 16 at line 66, In Claim 11, change "claim." to --claim--.

Signed and Sealed this
Third Day of May, 2016

Michelle K. Lee
*Director of the United States Patent and Trademark Office*